US010741053B2

(12) United States Patent
Newman et al.

(10) Patent No.: US 10,741,053 B2
(45) Date of Patent: *Aug. 11, 2020

(54) SYSTEMS AND METHODS FOR HEALTH MONITORING AND PROVIDING EMERGENCY SUPPORT

(71) Applicant: AMP LLC, Studio City, CA (US)

(72) Inventors: Fredric Mark Newman, Studio City, CA (US); Marsha Jo Newman, Studio City, CA (US)

(73) Assignee: AMP LLC, Studio City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,252

(22) Filed: May 24, 2019

(65) Prior Publication Data

US 2019/0281433 A1 Sep. 12, 2019

Related U.S. Application Data

(63) Continuation-in-part of application No. 15/618,487, filed on Jun. 9, 2017, now Pat. No. 10,304,315.

(60) Provisional application No. 62/348,113, filed on Jun. 9, 2016.

(51) Int. Cl.
| | |
|---|---|
| G08B 1/08 | (2006.01) |
| G08B 25/00 | (2006.01) |
| G08B 25/01 | (2006.01) |
| A61B 5/00 | (2006.01) |
| H04W 4/029 | (2018.01) |
| H04W 4/90 | (2018.01) |
| G08B 21/02 | (2006.01) |
| A61B 5/0205 | (2006.01) |
| A61B 5/145 | (2006.01) |

(52) U.S. Cl.
CPC ............ *G08B 25/001* (2013.01); *A61B 5/746* (2013.01); *G08B 21/02* (2013.01); *G08B 25/016* (2013.01); *H04W 4/029* (2018.02); *H04W 4/90* (2018.02); *A61B 5/02055* (2013.01); *A61B 5/14532* (2013.01); *A61B 5/747* (2013.01)

(58) Field of Classification Search
CPC ........ H04W 4/90; H04W 4/029; G08B 21/02; G08B 25/001; G08B 25/016; A61B 5/746; A61B 5/02055; A61B 5/14532; A61B 5/747
USPC .................................................... 340/539.12
See application file for complete search history.

(56) References Cited

U.S. PATENT DOCUMENTS 8,766,789 B2 * 7/2014 Cosentino ........... G06F 19/3418
340/539.12
8,862,393 B2 * 10/2014 Zhou ..................... G01S 5/0027
340/506

(Continued)

*Primary Examiner* — Zhen Y Wu
(74) *Attorney, Agent, or Firm* — Morgan, Lewis & Bockius LLP

(57) ABSTRACT

Systems and methods for providing a health monitoring and emergency response service are provided. Each element in a plurality of data elements is obtained from a health monitoring device connected to a corresponding subject in a plural of subjects. An alert is triggered through analysis of the data element or manually triggered by the subject or a subject's circle of support. The subject or one or more members of the circle of support of the subject verifies or rejects the alert. The alert is sent to a remote monitoring alarm center and emergency responders are dispatched.

20 Claims, 35 Drawing Sheets

(56) References Cited

U.S. PATENT DOCUMENTS

| | | | | |
|---|---|---|---|---|
| 8,942,676 B2* | 1/2015 | Dalton | G16H 80/00 | 455/414.1 |
| 9,374,698 B2* | 6/2016 | Ahmed | H04W 4/90 | |
| 10,055,803 B2* | 8/2018 | Orduna | G06Q 50/265 | |
| 10,347,369 B1* | 7/2019 | Dudzinski | G06Q 50/22 | |
| 2005/0151642 A1* | 7/2005 | Tupler | G08B 25/08 | 340/539.18 |
| 2006/0282021 A1* | 12/2006 | DeVaul | G08B 25/009 | 600/595 |
| 2008/0004904 A1* | 1/2008 | Tran | A61B 5/0006 | 705/2 |
| 2008/0166992 A1* | 7/2008 | Ricordi | A61B 5/0002 | 455/404.2 |
| 2009/0322513 A1* | 12/2009 | Hwang | A61B 5/02055 | 340/539.12 |
| 2010/0304709 A1* | 12/2010 | Riley | G08B 25/016 | 455/404.2 |
| 2012/0223833 A1* | 9/2012 | Thomas | G06F 19/3418 | 340/539.12 |
| 2013/0060167 A1* | 3/2013 | Dracup | A61B 5/11 | 600/595 |
| 2014/0079192 A1* | 3/2014 | Amerling | H04W 4/90 | 379/45 |
| 2014/0139616 A1* | 5/2014 | Pinter | A61B 5/0008 | 348/14.08 |
| 2014/0152453 A1* | 6/2014 | Dahl | G08B 25/005 | 340/686.6 |
| 2014/0273912 A1* | 9/2014 | Peh | H04W 4/90 | 455/404.1 |
| 2014/0278475 A1* | 9/2014 | Tran | G06F 19/3418 | 705/2 |
| 2015/0154847 A1* | 6/2015 | Oliver | H04W 4/80 | 340/686.6 |
| 2015/0161876 A1* | 6/2015 | Castillo | G08B 21/0453 | 340/539.11 |
| 2015/0173674 A1* | 6/2015 | Hayes | A61B 5/681 | 600/301 |
| 2015/0206418 A1* | 7/2015 | Hoffman | G08B 25/08 | 340/539.13 |
| 2015/0257653 A1* | 9/2015 | Hyde | A61B 5/021 | 600/473 |
| 2015/0279187 A1* | 10/2015 | Kranz | G08B 21/0415 | 340/539.12 |
| 2016/0038026 A1* | 2/2016 | Yang | A61B 5/1113 | 340/540 |
| 2016/0042637 A1* | 2/2016 | Cahill | G08B 25/10 | 701/3 |
| 2016/0071391 A1* | 3/2016 | Chang | G08B 25/016 | 340/539.11 |
| 2017/0358200 A1* | 12/2017 | Newman | A61B 5/746 | |
| 2018/0012471 A1* | 1/2018 | Bauer | H04L 67/1097 | |

* cited by examiner

SYSTEMS AND METHODS FOR HEALTH MONITORING AND PROVIDING EMERGENCY SUPPORT

CROSS-REFERENCE TO RELATED APPLICATIONS

The present application claims priority to U.S. patent application Ser. No. 15/618,487, filed on Jun. 9, 2017, entitled "Systems And Methods For Health Monitoring And Providing Emergency Support," now U.S. Pat. No. 10,304,315, which claims priority to U.S. Patent Application No. 62/348,113, filed on Jun. 9, 2016, entitled "A Health Monitoring Emergency Support, Command and Control System," the entire contents of which are hereby incorporated herein for all purposes by this reference.

TECHNICAL FIELD

The present disclosure generally relates to systems and methods for health monitoring and providing emergency support. More particularly, the present disclosure relates to a health monitoring emergency support, command, and control system designed to locally, and remotely through a support group, enable a subject to connect with emergency responders.

BACKGROUND

In general, a health monitoring emergency system enables a subject user to quickly connect with emergency services. With twenty-eight percent annual growth rate of baby boomers and an eighty percent chronic disease rate among senior citizens in the United States, emergency support platforms have become a growth industry that services nearly one billion people. However, even as the industry rapidly grows, society still depends on the old status quo options for emergency response.

Conventional emergency support platforms enable a subject to connect with a public-safety answering point (PSAP). Once in contact with the PSAP, emergency services are dispatched to the subject using a predetermined location provided by the subject, or the subject communicates their location to the PSAP.

When a subject is not at a predetermined location or is not capable of communicating with the PSAP the conventional emergency support platforms fail. There exists a need for a subject to communicate their real time location in the event of an emergency.

Another drawback with conventional emergency support platforms is that they do not provide satisfactory ways for a subject to verify or cancel an alert once the alert has been activated. When a false alert is activated, emergency responders waste precious time and resources that could have been allocated to an actual emergency and patient, while the subject is charged for the cost of the emergency dispatch.

Still another drawback with conventional emergency support platforms is that the circle of support (CoS) for a subject has no means for receiving information regarding an emergency or verifying if the emergency is real or not. A subject's circle of support includes the persons the subject most readily identifies with and whom know the subject's and their medical history best. When a subject is not capable of communicating, the subject's circle of support cannot assist in any fashion using conventional emergency support systems.

Thus, prior to the present disclosure there existed a need for improved emergency support platforms that streamlines the process of dispatching emergency responders, engaging a subject's circle of support, and supplying the emergency responders with critical patient medical information while minimizing or eliminating the number of false calls.

The information disclosed in this background section is only for enhancement of understanding of the general background of the invention and should not be taken as an acknowledgement or any form of suggestion that this information forms the prior art already known to a person skilled in the art.

SUMMARY

Advantageously, the detailed in the present disclosure address the shortcomings in the prior art detailed above.

Various aspects of the present disclosure are directed to providing a health monitoring emergency support, command, and control system.

One aspect of the present disclosure provides a computer system for providing a health monitoring and emergency support service to a plurality of subjects. The computer system includes a first computer including one or more first processors and a first memory. The first memory includes first non-transitory instructions, which, when executed by the one or more first processors, performs a first method. The first method includes running a monitoring process. The monitoring process includes polling for a data element in a plurality of data elements from a health monitoring device in a plurality of health monitoring devices associated with the respective subject. A first notification process is initiated for a candidate subject in the plurality of subjects when a data element satisfies a first alarm trigger condition. The first notification process, which is performed for the candidate subject when the respective data element satisfies the first alarm trigger condition, includes notifying a remote alarm monitoring center about the first alarm trigger condition and a current location of the candidate subject. A second notification process is initiated for the candidate subject when the respective data element satisfies a second alarm trigger condition. The second notification process, performed for the candidate subject when the respective data element satisfies the second alarm trigger condition, includes communicating the data element or the second alarm trigger condition to each remote device in a plurality of remote devices. Each remote device in the plurality of remote devices is associated with a support member in a plurality of support members that is uniquely associated with the candidate subject. The second notification process further includes communicating the data element or the second alarm trigger condition to the health monitoring device associated with the candidate subject. The second notification process further includes concurrently polling for a verification response from the plurality of remote devices and the health monitoring device associated with the candidate subject. Responsive to receiving the verification response from either any one or more remote devices in the plurality of remote devices or from and the health monitoring device associated with the candidate subject, a third notification process is initiated. The third notification process notifies the remote alarm monitoring center about the second alarm trigger condition and the current location of the candidate subject when the verification response satisfies a first condition. The second notification process is terminated when the verification response satisfies a second condition without notifying the remote alarm monitoring center about the second alarm trigger condition. The first condition is satisfied in accordance with a determination that a most recently received verification response from one or more remote devices in the plurality of remote devices is a confirmation. The first condition is also satisfied in accordance with a determination that a most recently received verification response from the health monitoring device associated with the candidate subject is a confirmation. Additionally, the second condition is satisfied in accordance with a determination that a most recently received verification response from either any one or more remote devices in the plurality of remote devices or the health monitoring device associated with the candidate subject is a rejection.

In some embodiments, the first notification process further includes communicating the data element or the first alarm trigger condition to each remote device in the plurality of remote devices.

In some embodiments, satisfying the first alarm trigger condition includes through one or more commands by either the candidate subject or a respective remote device in the plurality of remote devices.

In some embodiments, the polling further includes instructions for receiving an interrupt communication from the candidate subject. When the interrupt communication from the candidate subject is received within a predetermined time period of receiving the respective data element for the candidate subject, the respective notification process and the respective alarm trigger condition are cancelled.

In some embodiments, the instructions for receiving the interrupt communication from the candidate subject further includes: when the interrupt communication from the candidate subject is not received the predetermined time period of receiving the respective data element for the candidate subject, a communication channel is opened between the candidate subject and the remote alarm monitoring center.

In some embodiments, the communication channel requires entry of a password in order to remain open. In some embodiments, the interrupt communication from the candidate subject is confirmed through entry of the password. In some embodiments, the password is a spoken safe word.

In some embodiments, the current location of the candidate subject includes a set of geographical coordinates including a latitude, a longitude, and/or an elevation. In some embodiments, the current location of the candidate subject includes a physical address. Furthermore, in some embodiments, the current location of the candidate subject includes one or more instructions provided by the candidate subject.

In some embodiments, the notifying the remote alarm monitoring center includes providing the current location of the candidate subject on a recurring basis.

In some embodiments, the second notification process further includes creating a communication channel between the candidate subject and each respective support member in the plurality of support members independent of a location of the respective support member responsive to the alarm trigger condition, wherein the communication channel allows for the candidate subject and a respective support member to directly communicate with each other. In some embodiments, the second notification process further includes creating a communication channel between the candidate subject and the remote alarm monitoring center responsive to the alarm trigger condition, wherein the communication channel allows for the candidate subject and the remote alarm monitoring center to directly communicate with each other.

In some embodiments, the third notification process further includes creating a communication channel between the candidate subject and the remote alarm monitoring center responsive to the alarm trigger condition, wherein the communication channel allows for the candidate subject and the remote alarm monitoring center to directly communicate with each other. In some embodiments, the third notification process further includes communicating a plurality of medical information related to the candidate subject to each remote device in the plurality of remote devices and the health monitoring device associated with the candidate subject. In some embodiments, the plurality of medical information is provided through a link to a third-party website.

In some embodiments, the first notification process further includes notifying the remote alarm monitoring center about a state of a volume setting of the health monitoring device.

Another aspect of the present disclosure provides a computer system for providing a health monitoring and emergency support service to a plurality of subjects. The computer system includes a computer including one or more processors and a memory. The memory includes non-transitory instructions, which, when executed by the one or more processors, performs a method. The method includes running a monitoring process. The monitoring process includes polling for a data element in a plurality of data elements from a health monitoring device in a plurality of health monitoring devices each uniquely associated with a corresponding subject. A notification process is initiated for a candidate subject in the plurality of subjects when a respective data element satisfies an alarm trigger condition. The notification process, performed for the candidate subject in the plurality of subjects when the respective data element satisfies the alarm trigger condition, includes notifying a remote alarm monitoring center about the alarm trigger condition and a current location of the candidate subject.

A further aspect of the present disclosure provides a computer system for providing a health monitoring and emergency support service to a plurality of subjects. The computer system includes a computer including one or more processors and a memory. The memory includes non-transitory instructions, which, when executed by the one or more processors, performs a method. The method includes running a monitoring process. The monitoring process includes polling for a data element in a plurality of data elements from a health monitoring device in a plurality of health monitoring devices each uniquely associated with a corresponding subject. A notification process is initiated for a candidate subject in the plurality of subjects when a respective data element satisfies an alarm trigger condition. The notification process, performed for the candidate subject in the plurality of subjects when the respective data element satisfies the alarm trigger condition, includes notifying a remote alarm monitoring center about the alarm trigger condition and a current location of the candidate subject, and opening a communication channel between the candidate subject and the remote alarm monitoring center.

Yet another aspect of the present disclosure provides a non-transitory computer readable storage medium, where the non-transitory computer readable storage medium stores instructions, which when executed by a computer system, cause the computer system to perform any of the methods for providing a health monitoring and emergency support service described in the present disclosure.

In accordance with an aspect of the present disclosure, the above and other objects can be accomplished by the provision of a health monitoring and emergency support service which streamlines the process of dispatching emergency responders and engages a subject's circle of support.

The methods and apparatuses of the present disclosure have other features and advantages which will be apparent from or are set forth in more detail in the accompanying drawings, which are incorporated herein, and the following Detailed Description, which together serve to explain certain principles of the present invention.

Figure 1:
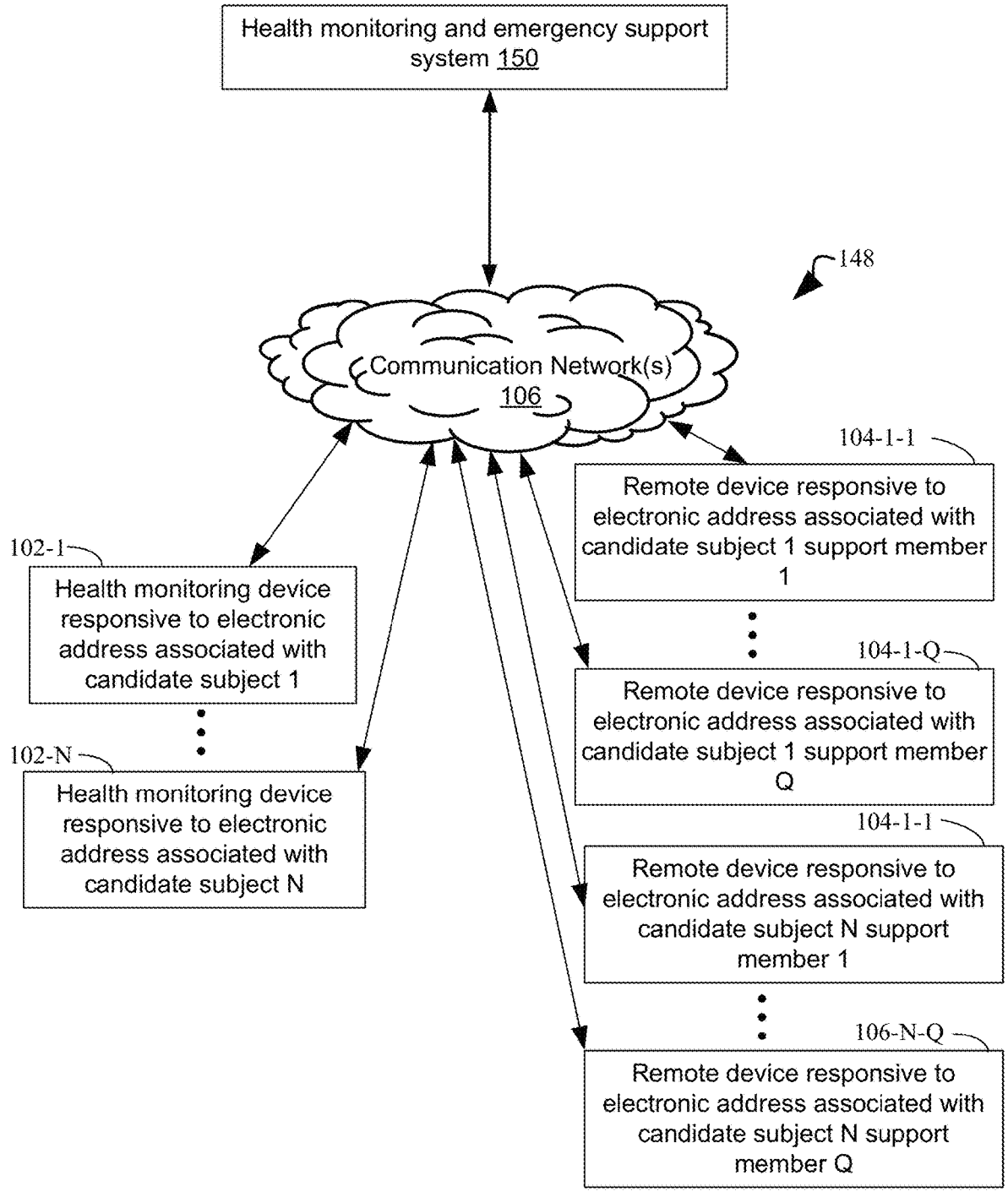
FIG. 1 illustrates an exemplary system topology including a health monitoring and emergency support system in accordance with an exemplary embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

In the United States, both the population and the median age of residents continue to increase yearly (Colby et al., 2017, "Projections of the size and composition of the US population: 2014 to 2060: Population estimates and projections," Print). With age the health of a resident deteriorates, leading to increased hospitalizations and visits to medical practitioners (Center for Disease Control and Prevention, 2015, "Visits to physician offices, hospital outpatient departments, and hospital emergency departments, by age, sex, and race: United States, selected years 1995-2011," Print). However, transporting and caring for residents in emergency situations consumes valuable resources emergency responders, and many calls for emergency responders are false alarms (Blackstone et al., 2007, "The economics of emergency response." Policy Sciences, 40(4), pg. 313.).

To address this, the systems and methods of the present disclosure provide a health monitoring and emergency response service. The health monitoring and emergency response service obtains a data element in a plurality of data elements from a health monitoring device associated with a subject in a plural of subjects. An alert is triggered through analysis of the data element or, alternatively, manually triggered by either the subject or a member of the subject's support group (e.g., circle of support). The subject or one or more members of the circle of support can verify or reject the alert, preventing false alarms from being communicated to emergency responders if the alert is unnecessarily triggered. If the alert is not a false alarm, the alert is communicated to a remote monitoring alarm center. The remote alarm monitoring center optionally decides to dispatch emergency responders to a current location of the subject. Accordingly, the health monitoring and emergency response service allows the circle of support to dispatch emergency responders to the current location of the subject from a remote location even if the subject is incapacitated.

Reference will now be made in detail to various embodiments of the present disclosure, examples of which are illustrated in the accompanying drawing and described below. While the disclosure will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. The terms "subject" and "user" are used interchangeably herein. Furthermore, unless stated otherwise, the terms "alert" and "alarm" are used interchangeably herein.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

An aspect of the present disclosure is directed to providing a health monitoring and emergency support service. Systems and methods for providing a health monitoring and emergency response service are provided. The systems and methods include obtaining a data element in a plurality of data elements from a health monitoring device or a remote device. The health monitoring device is associated with a subject in a plural of subjects, and each remote device is associated with a support member further associated with the subject. An alert is triggered through analysis of the data element or, alternatively, manually triggered by the subject or support member associated with the subject. The subject or one or more support members associated with the subject verifies or rejects the alert. The alert is communicated to a remote monitoring alarm center, and emergency responders are dispatched.

FIG. 1 illustrates an exemplary topography of an integrated system 148 for the acquisition of data elements. The integrated system 148 includes one or more health monitoring devices 102 that communicate the various data elements throughout the system. Each health monitoring devices 102 is associated with a subject (e.g., a first health monitoring device 102-1 is associated with a first subject). The integrated system 148 also includes one or more remote devices 104, each associated with a different support member that is further associated with a respective subject. Furthermore, the integrated system 148 includes a health monitoring and emergency support system 150 that at least manages communication between the various components and devices of the system 148 and polls for data elements therefrom (e.g., the health monitoring devices 102, the remote devices 104, emergency responders, an auxiliary server, etc.).

With the integrated system 148, data elements from the health monitoring devices 102 (e.g., medical devices) of the various subjects are obtained. Each data element includes a condition of the health monitoring device 102 (e.g., a current location associated with the health monitoring device, a state of a setting of the health monitoring device such as a volume indicator 510 of FIG. 5) or a condition of the corresponding subject measured by the health monitoring device (e.g., a glucose measurement of the subject). In some embodiments, one or more data elements is used to determine if an alert and/or alarm is triggered.

Figure 2A:
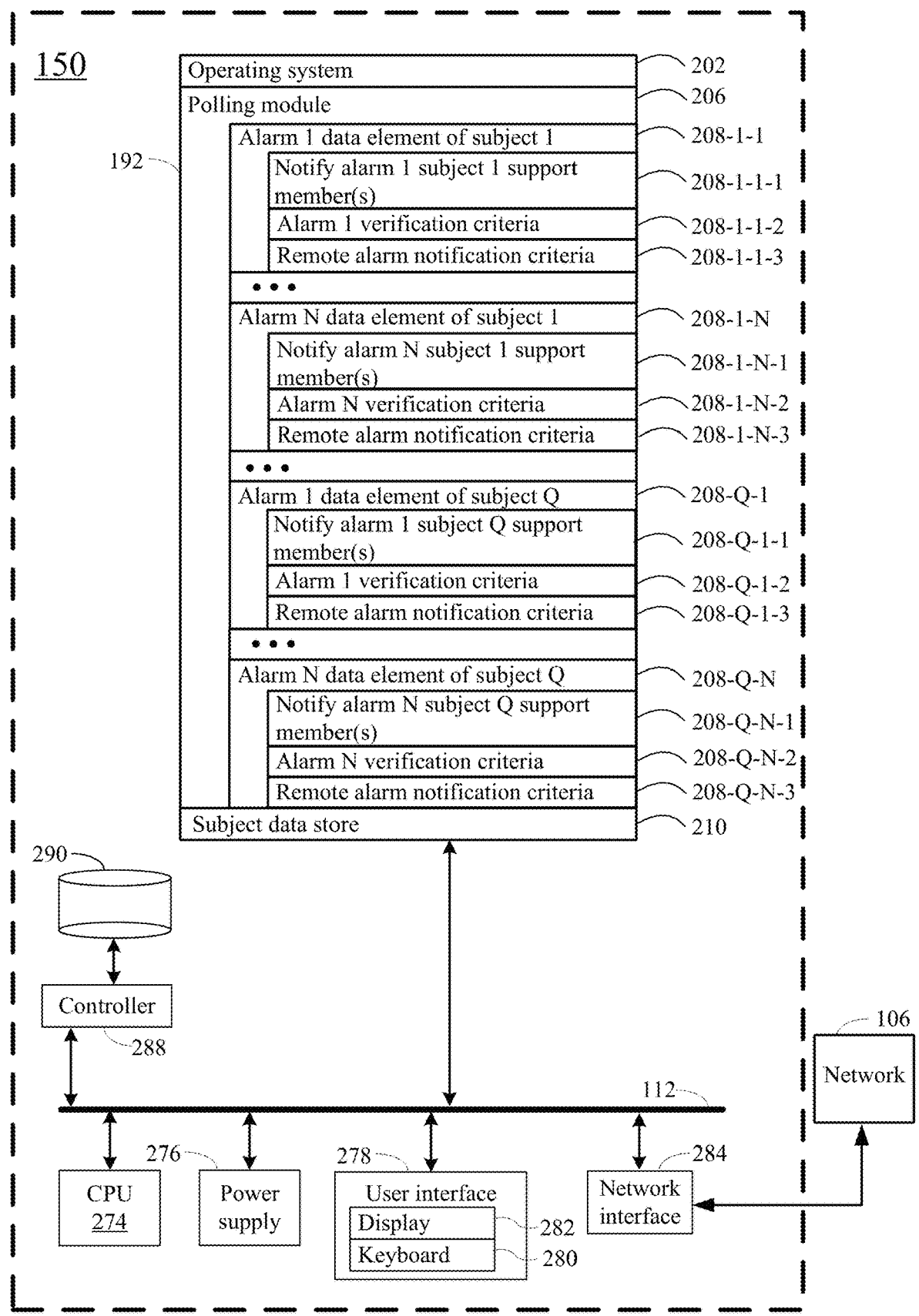
FIGS. 2A and 2B collectively illustrate a health monitoring emergency support system in accordance with an exemplary embodiment of the present disclosure.
Figure 2B:
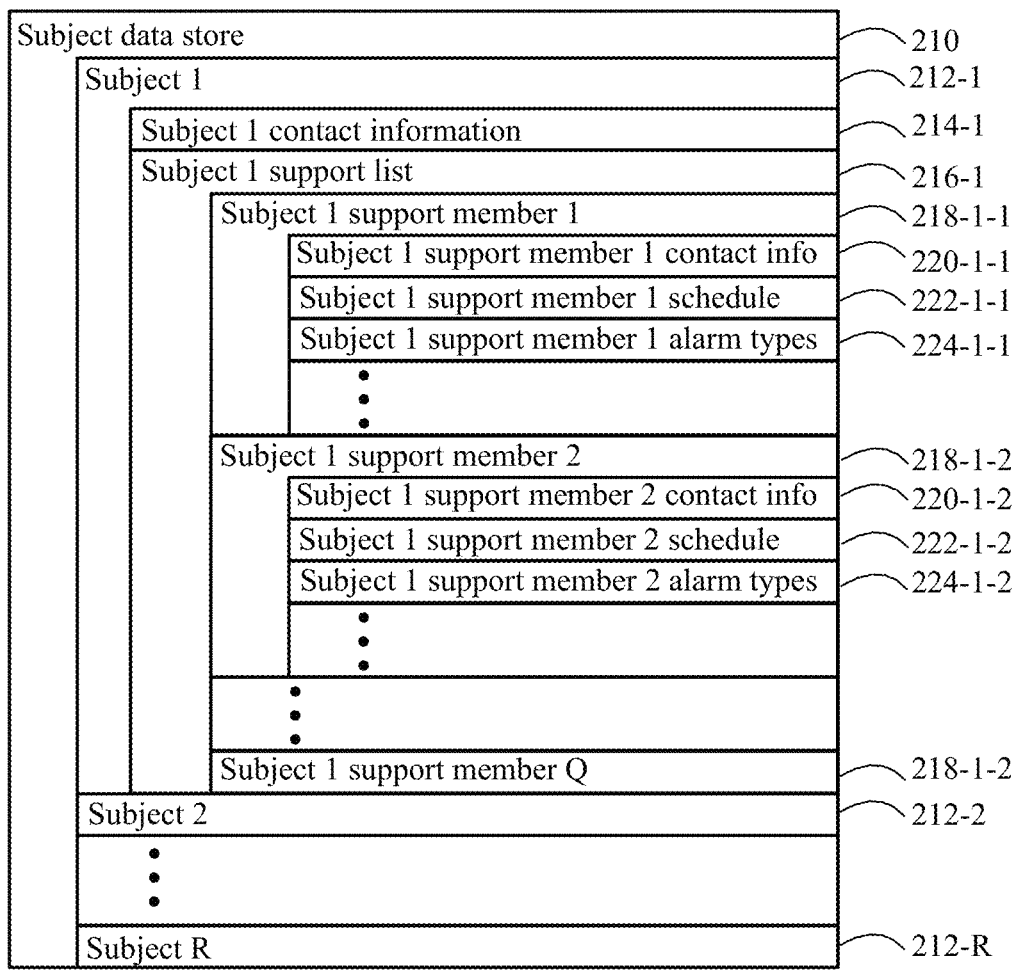
Figure 3:
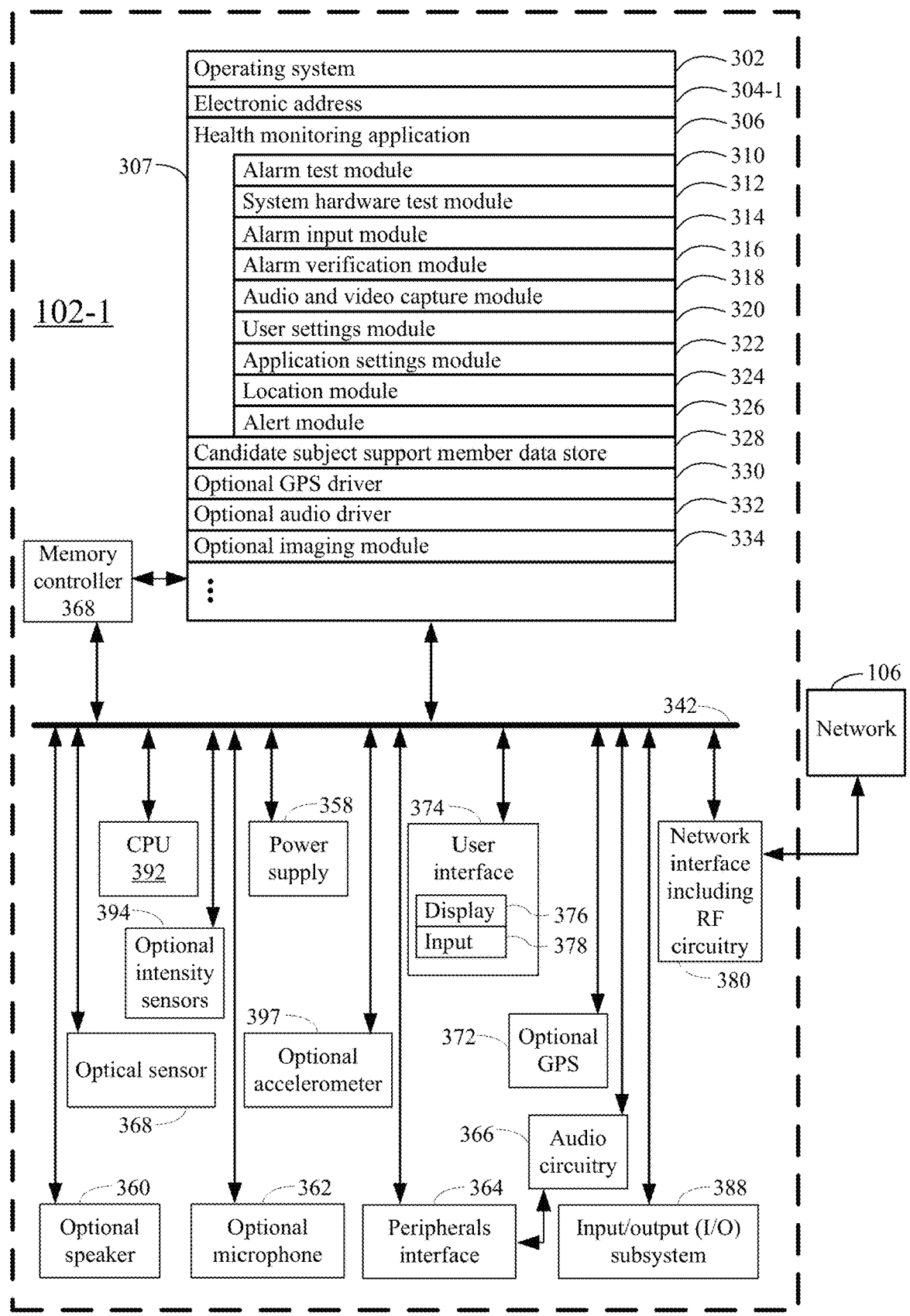
FIG. 3 illustrates various modules and/or components of a health monitoring emergency support application in accordance with exemplary embodiment of the present disclosure.

A detailed description of a system 148 for providing a health monitoring and emergency support service in accordance with the present disclosure is described in conjunction with FIG. 1 through FIG. 3. As such, FIG. 1 through FIG. 3 collectively illustrate an exemplary topology of the system 148 in accordance with the present disclosure. In the topology, there is a health monitoring and emergency support system 150 for receiving a variety of data elements from a plurality of subjects. The health monitoring and emergency support system 150 utilizes the one or more data elements to ascertain an alert trigger condition ("health monitoring and emergency support system 150") (FIG. 1 and FIG. 2). The system 148 also includes one or more health monitoring devices 102 associated with each subject (FIG. 1), and one or more remote devices 104 associated with a support member further associated with a subject (FIG. 1).

Referring to FIG. 1, the health monitoring and emergency support system 150 is configured to determine an alert trigger condition. In determining the alert trigger condition, the health monitoring and emergency support system 150 receives one or more data elements originating from one or more health monitoring devices 102 and/or one or more remote devices 104 that have been provided to, and/or associated with, a corresponding subject. Each such data element includes a condition of the health monitoring device 102 or a condition of the corresponding subject that was determined, at least in part, by the health monitoring device 102. In some embodiments, a data element includes information identifying a source of the data element (e.g., a first data element includes information identifying a first health monitoring device as the source).

In some embodiments, the health monitoring and emergency support system 150 receives the data element wirelessly through radio-frequency signals. In some embodiments, such signals are in accordance with an 802.11 (Wi-Fi), Bluetooth, or ZigBee standard.

In some embodiments, the health monitoring and emergency support system 150 receives a data elements directly (e.g., directly from a health monitoring device 102). In some embodiments, the health monitoring and emergency support system 150 receives a data element from an auxiliary server. In such embodiments, the auxiliary server is in communication with a health monitoring device 102 and receives one or more data elements from the health monitoring device. The auxiliary server analyzes the data elements received from the health monitoring device 102 and communicates the analyzed data elements to the health monitoring and emergency support system 150. For instance, in some embodiments a data element received from a health monitoring device 102 includes unprocessed physiological data (e.g., a data element from an electrocardiogram (EKG)) associated with a subject (e.g., a candidate subject). Accordingly, the auxiliary server analyzes the data elements to determine if an alert trigger condition is satisfied. In some embodiments, the analysis conducted by the auxiliary server includes determining if a predetermined threshold criterion has been satisfied by a data element (e.g., a sudden change in measured value associated with the health of the subject, a change in trend of a value associated with the health of the subject, a measured value that satisfies a ceiling threshold value, etc.). In some embodiments, a medical practitioner provides the predetermined threshold criterion. In some embodiments, the predetermined threshold criterion is determined according to a set of healthcare guidelines, which may change over time, and/or vary on a jurisdiction-by-jurisdiction basis. For example, in the United States, the American College of Cardiology and the American Heart Association collaborated to provide guidance on management of high blood pressure, which may be the basis for determining threshold criterion of an alert trigger condition. Whelton P K, et al., J Am Coll Cardiol., S0735-1097(17) 41519-1 (2017).

In some embodiments, the health monitoring and emergency support system 150 receives the data elements indirectly. In some embodiments, a health monitoring device 102 is and/or includes an external device, such as a measurement device (e.g., a glucose sensor, a heart rate monitor, etc.), that communicates with a further device associated with the subject (e.g., shares a Bluetooth connection to a smart phone associated with a subject). For instance, in some embodiments the external device includes a conductive energy weapon, or similar self-defense device, that communicates with the health monitoring device 102 (e.g., the conductive energy weapon has a Bluetooth connection with the health monitoring device). In some embodiments, the health monitoring device 102 communicates a signal indicative of the health of the subject (e.g., a condition of a data element) to the smart phone, which, in turn, communicates the signal to the health monitoring and emergency support system 150. In some embodiments, the smart phone analyzes the signal from the health monitoring device 102 and only communicates a data element to the health monitoring and emergency support system 150 when a predetermined threshold criterion has been satisfied (e.g., a sudden change in measured value associated with the health of the subject, a change in trend of a value associated with the health of the subject, etc.). In some such embodiments, there are any number of intermediate hops between the measurement device 102 and the health monitoring and emergency support system 150. For instance, in some embodiments after the health monitoring device 102 has reported to (e.g., communicated with) a smart phone associated with the subject, the data element is communicated to any number of intermediate servers (e.g., an auxiliary server) for further analysis prior to communicating the data element to the health monitoring emergency support system 150.

In some embodiments, more than one health monitoring device 102 is associated with a respective subject. For instance, in some embodiments a first health monitoring device 102-1 is configured to monitor a first physiological measurement related to the health of the subject (e.g., condition of a data element), and a second health monitoring device 102-2 is configured to measure a second physiological measurement related to the health of the subject (e.g., the first health monitoring device 102-1 measures a pulse of the subject and the second health monitoring device 102-2 measures a glucose level of the subject). In some embodiments, any number of trend analysis or threshold alerts are set to monitor these measurements in order to determine whether to fire an alert to the health monitoring and emergency support system 150 in the form of a data element.

In some embodiments, the health monitoring and emergency support system 150 is not proximate to the subject and/or does not have wireless capabilities or such wireless capabilities are not used for the purpose of acquiring a data element. In such embodiments, a communication network 106 is utilized to communicate a data element from a health monitoring device 102 or a remote device 104 to the health monitoring and emergency support system 150.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoW), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 148 other than the one depicted in FIG. 1 are possible. For instance, in some embodiments rather than relying on a communications network 106, the one or more health monitoring devices 102 wirelessly transmit information directly to the health monitoring system 250. Further, in some embodiments the health monitoring and emergency support system 150 constitute a portable electronic device, a server computer, or in fact constitute several computers that are linked together in a network, or be a virtual machine and/or a container in a cloud-computing context. As such, the exemplary topology shown in FIG. 1 merely serves to describe the features of an embodiment of the present disclosure in a manner that will be readily understood to one of skill in the art.

Turning to FIG. 2 with the foregoing in mind, in some embodiments the health monitoring and emergency support system 150 includes one or more computers. For purposes of illustration in FIG. 2, the health monitoring and emergency support system 150 is represented as a single computer that includes all of the functionality for providing a health monitoring and emergency support system. However, the present disclosure is not limited thereto. In some embodiments, the functionality for providing a health monitoring and support system 150 is spread across any number of networked computers, and/or resides on each of several networked computers, and/or is hosted on one or more virtual machines and/or one or more containers at a remote location accessible across the communications network 106. One of skill in the art will appreciate that any of a wide array of different computer topologies are used for the application and all such topologies are within the scope of the present disclosure.

An exemplary health monitoring and emergency support system 150 for providing a health monitoring and emergency support system is depicted in FIG. 2. The health monitoring and emergency support system 150 includes one or more processing units (CPU's) 274, a network or other communications interface 284, a memory 192 (e.g., random access memory), one or more magnetic disk storage and or persistent devices 290 optionally accessed by one or more controllers 288, one or more communication busses 112 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and or memory 290 includes mass storage that is remotely located with respect to the central processing unit(s) 274. In other words, some data stored in memory 192 and/or memory 290 may in fact be hosted on computers that are external to the health monitoring and emergency support system 150 but that can be electronically accessed by the health monitoring and emergency support system 150 over an Internet, intranet, or other form of network or electronic cable (illustrated as element 106 in FIG. 2) using network interface 284.

In some embodiments, the memory 192 of the health monitoring and emergency support system 150 for providing emergency support stores:

an operating system 202 that includes procedures for handling various basic system services;

a polling module 206 that facilitates polling for various alarm data elements from the health monitoring devices 102 and/or the remote devices 104;

a subject data store 210 that stores a plurality of subject records 212, where each respective subject record 212 in the plurality of subject records is associated with a corresponding subject and stores at least subject contact information 214 and a subject support list 216 that includes contact information 220 of each remote device 104 associated with the corresponding subject, support member schedules 222 for providing an availability schedule of the support members, and a support member alarm type 224 which associates each support member 218 with one or more specific alarm types (e.g., specific emergency types).

In some embodiments, the polling module 206 runs on native device frameworks, and is available for download onto the health monitoring and emergency support system 150 running an operating system 202 (e.g., an operating system such as Android or iOS as well as Linux, Windows, etc.). In some embodiments, the polling module 206 polls for data elements 208 from the health monitoring devices 102 and/or the remote devices 104 on a continuous basis or on a recurring basis (e.g., every second, every 10 seconds, every 30 seconds, every 60 seconds, every 120 seconds, every 180 seconds, etc.). In some embodiments, the polling for data elements 208 occurs depending on if an alarm is triggered from a health monitoring device 102. For instance, if a health monitoring device 102 triggers an alarm the polling module 206, in some embodiments, polls for data elements from the health monitoring device more often than a different health monitoring devices.

Figure 23:
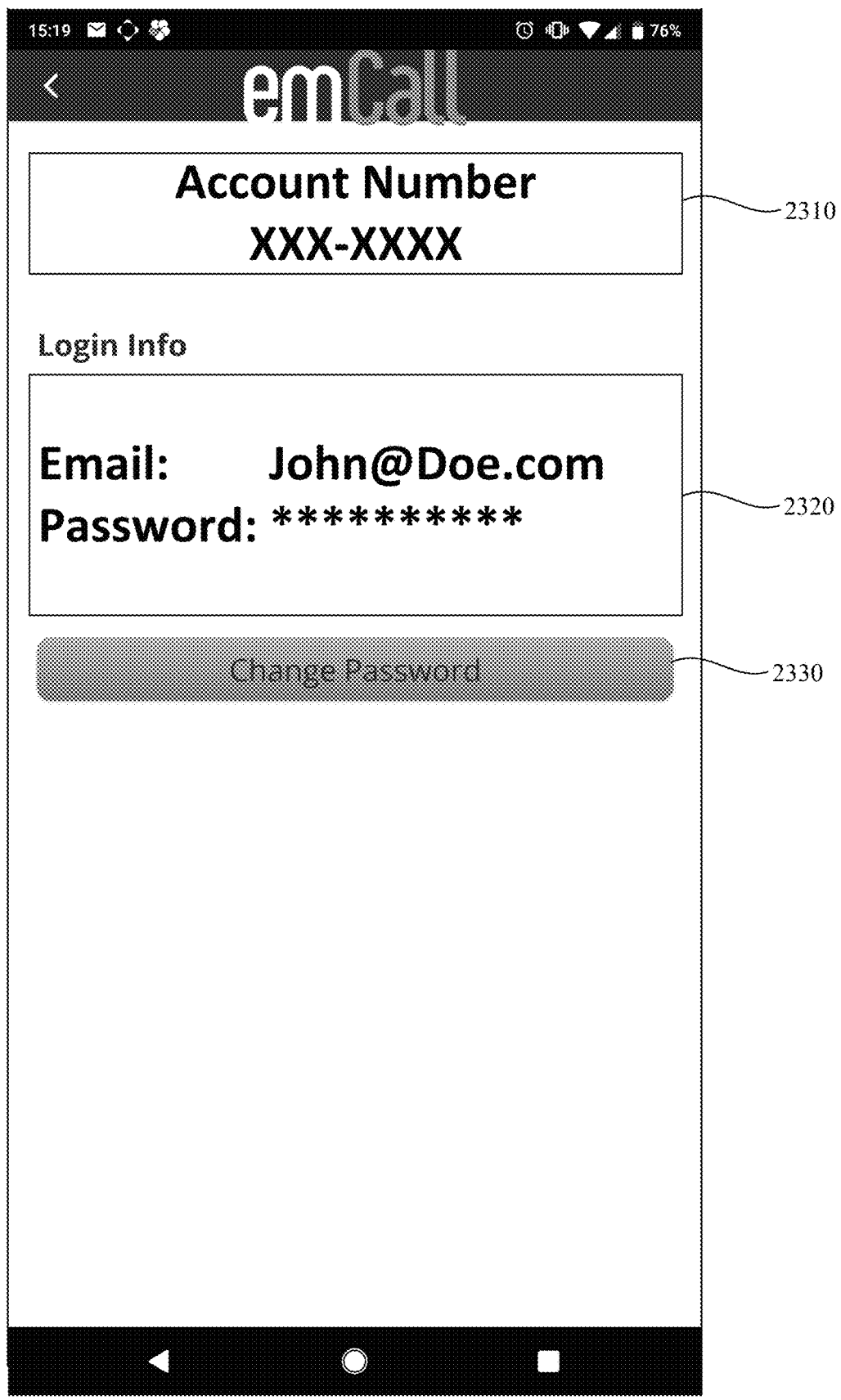
FIG. 23 illustrates a user interface for modifying a user profile in accordance with an exemplary embodiment of the present disclosure.

In some embodiments, each alarm data element 208 includes a notification and/or identifier that identifies the corresponding health monitoring device 102 and/or remote device 104 from which the respective data element originates. This identifier of the originating health monitoring device 102 includes an electronic address of the respective device (e.g., electronic address 304 of FIG. 3), an account identifier associated with an end-user of the respective device (e.g., account identifier 2310 of FIG. 23), a serial number that optionally includes a model number and/or manufacturer of the respective device, or a combination thereof. For instance, in some embodiments, the health monitoring device 102 is in communication with an external device (e.g., a glucose monitor device, a conductive energy weapon device, etc.) and a data elements includes a notification identifying the external device as the source of the triggering of the data element.

In some embodiments, each alarm data element 208 includes one or more health monitoring device 102 diagnostic conditions. Further, in some embodiments, each data element 208 includes one or more measurements obtained from the health monitoring device 102. The one or more measurements include measurements taking from one or more sensors of the health monitoring device (e.g., optical sensor 368, intensity sensors 394, and/or accelerometer 397 of FIG. 3, etc.), including a blood pressure measurement, a heart rate measurement, a glucose measurement, a temperature of the subject (e.g., a core temperature, a temporal temperature, etc.).

In some embodiments, one or more of the above identified data elements 208 and/or modules of the health monitoring and emergency support system 150 are stored in one or more of the previously described memory devices (e.g., memory 192 and/or memory 290), and correspond to a set of instructions for performing a function described above. The above-identified data, modules, or programs (e.g., sets of instructions) need not be implemented as separate software programs, procedures, or modules. Thus, various subsets of these modules may be combined or otherwise re-arranged in various implementations. In some implementations, the memory 192 and/or memory 290 optionally stores a subset of the modules and data structures identified above. Furthermore, in some embodiments the memory 192 and/or memory 290 stores additional modules and data structures not described above.

Referring to FIG. 3, a description of an exemplary health monitoring device 102-1 that can be used with the presently disclosure is provided. In the present embodiment, an exemplary health monitoring device 102 and an exemplary remote device 104 utilize the same hardware and can be considered or the same type of device (e.g., both devices are of the smart phone type). Unless stated otherwise, the hardware features of a respective health monitoring device 102 are the same for a respective remote device 104.

In some embodiments, a health monitoring device 102 and/or a remote device 104 is a smart phone (e.g., an iPhone, an Android smart phone, etc.), a laptop computer, a tablet computer, a desktop computer, or another form of electronic device (e.g., a gaming console, a stand-alone device). However, the present disclosure is not limited thereto. For instance, in some embodiments a health monitoring device 102 is an implantable device (e.g., some or all of the health monitoring device is implanted in the corresponding subject), such as an implantable cardiac device (e.g., a pacemaker) or an insulin pump. In some embodiments, the corresponding health monitoring device 102 is a wearable smart device utilized by a respective subject. Wearable health monitoring devices 102 include smart devices, such as a smart watch or smart glasses, as well as wearable medical devices, such as a heart rate monitor device or a blood pressure monitor device. In some embodiments, a respective health monitoring device 102 is not worn by or implanted in the corresponding subject (e.g., the corresponding monitoring device is proximate to the corresponding subject, such as a smart phone device or a conductive energy weapon device). Furthermore, in some embodiments a respective health monitoring device is an emergency vehicle computer or another form of a wired or wireless networked device.

The health monitoring device 102 illustrated in FIG. 3 has one or more processing units (CPU's) 392, peripherals interface 364, memory controller 368, a network or other communications interface 380, a memory 307 (e.g., random access memory), a user interface 374, the user interface 374 including a display 376 and input 378 (e.g., keyboard, keypad, touch screen), an optional accelerometer 397, an optional GPS 372, optional audio circuitry 366, an optional speaker 360, an optional microphone 362, one or more optional intensity sensors 394, an optional input/output (I/O) subsystem 388, one or more optional optical sensors 368, one or more communication busses 342 for interconnecting the aforementioned components, and a power supply 358 for powering the aforementioned components.

In some embodiments, the input 378 is a touch-sensitive display, such as a touch-sensitive surface. In some embodiments, the user interface 374 includes one or more soft keyboard embodiments. In some embodiments, the soft keyboard embodiments include standard (QWERTY) and or non-standard configurations of symbols on the displayed icons. Nevertheless, the input 378 and/or the user interface 374 is utilized by an end-user of the respective health monitoring device 102 (e.g., a respective subject) to input various commands (e.g., push commands) to the respective device.

The health monitoring device 102 illustrated in FIG. 3 optionally includes, in addition to accelerometer(s) 397, a magnetometer, and a global positioning system (GPS) 372 (or GLONASS or other global navigation system) receiver for obtaining information concerning a current location (e.g., a latitude, a longitude, an elevation, etc.) and/or an orientation (e.g., a portrait or a landscape orientation of the device) of the health monitoring device 102 and/or for determining an amount of physical exertion by the subject (e.g., a rate of change of a current location, a rate of change of a current location with respect to a heart rate of the subject, etc.).

It should be appreciated that the health monitoring device 102 illustrated in FIG. 3 is only one example of a multi-function device that may be used for collecting data elements 208 from the health monitoring device(s) 102 of a corresponding subject or the remote device(s) 104 of a corresponding support member. Thus, the health monitoring device 102 and/or the remote device 104 optionally has more or fewer components than shown, optionally combines two or more components, or optionally has a different configuration or arrangement of the components. In fact, as discussed above, in some embodiments, a data element 208 is acquired by the health monitoring and emergency support system 150 directly from the health monitoring device 102 and/or the remote device 104. The various components shown in FIG. 3 are implemented in hardware, software, firmware, or a combination thereof, including one or more signal processing and/or application specific integrated circuits.

Memory 307 of the health monitoring device 102 illustrated in FIG. 3 optionally includes high-speed random access memory and optionally also includes non-volatile memory, such as one or more magnetic disk storage devices, flash memory devices, or other non-volatile solid-state memory devices. Access to memory 307 by other components of the health monitoring device 102, such as CPU(s) 392 is, optionally, controlled by the memory controller 368.

In some embodiments, the data elements 208 of FIG. 2 include a plurality of physiological measurements, and each such physiological measurement includes a measurement value. In some embodiments, the physiological measurement is a temperature of the subject (e.g., a core temperature, a temporal temperature, a tympanic temperature, an axillary temperature, an oral temperature, etc.). In some embodiments, the physiological measurement is a measurement of activity of the subject (e.g., a distanced traveled per period of time). In some embodiments, these physiological measurements serve as additional data, in addition to that provided by the health monitoring devices 102 found in acquired data elements 208 associated with a subject. In some embodiments, these physiological measurements serve to verify or help to determine a condition of the corresponding subject in conjunction with the data from the health monitoring devices 102. In some embodiments, the optional accelerometer 317, optional GPS 319, and/or magnetometer of the health monitoring device 102 or such components acquire such physiological measurements.

In some embodiments, the peripherals interface 364 couples input and output peripherals of the device to the CPU(s) 392 and the memory 307. The one or more CPU(s) 392 run or execute various software programs and/or sets of instructions stored in the memory 307, such as the health monitoring application 306, to perform various functions for the health monitoring device 102 and process data.

In some embodiments, the peripherals interface 364, the CPU(s) 392, and the memory controller 368 are implemented on a single chip. In some other embodiments, the peripherals interface 364, the CPU(s) 392, and the memory controller 368 are implemented on separate chips.

RF (radio frequency) circuitry of network interface 380 receives and sends RF signals, also called electromagnetic signals. In some embodiments, the data elements 208 are received using the present RF circuitry from one or more devices such as a health monitoring device 102 associated with a subject or a remote device 104. In some embodiments, the RF circuitry 380 converts electrical signals to from electromagnetic signals and communicates with communications networks and other communications devices, health monitoring devices 102, remote devices 104, and or the health monitoring and emergency support system 150 via the electromagnetic signals. The RF circuitry 380 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 380 optionally communicates with the communication network 106. In some embodiments, the circuitry 380 does not include RF circuitry and, in fact, is connected to the network 106 through one or more hard wires (e.g., an optical cable, a coaxial cable, or the like).

In some embodiments, the audio circuitry 366, the optional speaker 360, and the optional microphone 362 provide an audio interface between the subject and the health monitoring device 102, enabling the health monitoring device to provide communication channels between the subject and another entity (e.g., a remote device, the health monitoring and emergency support system 150, a health monitoring device 102, an emergency responder, etc.). The audio circuitry 366 receives audio data from the peripherals interface 364, converts the audio data to electrical signals, and transmits the electrical signals to the speaker 360. The speaker 360 converts the electrical signals to human-audible sound waves. The audio circuitry 366 also receives electrical signals converted by the microphone 362 from sound waves. The audio circuitry 366 converts the electrical signal to audio data and transmits the audio data to peripherals interface 364 for processing. Audio data is, optionally, retrieved from and or transmitted to the memory 307 and or the RF circuitry 380 by the peripherals interface 364.

In some embodiments, the power supply 358 optionally includes a power management system, one or more power sources (e.g., one or more batteries, alternating current (AC)), a recharging system, a power failure detection circuit, a power converter or inverter, a power status indicator (e.g., a light-emitting diode (LED)) and any other components associated with the generation, management, and distribution of power in portable devices.

In some embodiments, the health monitoring device 102 optionally also includes one or more optical sensors 368. The optical sensor(s) 368 optionally include charge-coupled device (CCD) or complementary metal-oxide semiconductor (CMOS) phototransistors. The optical sensor(s) 368 receive light from the environment, projected through one or more lens, and converts the light to data representing an image. The optical sensor(s) 368 optionally capture still images and or video. In some embodiments, an optical sensor is disposed on a back end portion of the health monitoring device 102 (e.g., opposite the display 376 on a front end portion of the health monitoring device 102) so that the input 378 is enabled for use as a viewfinder for still and or video image acquisition. In some embodiments, another optical sensor 368 is located on the front end portion of the health monitoring device 102 so that an image of the subject is obtained (e.g., to verify the health or condition of the subject, to determine the physical activity level of the subject, to help diagnose a subject's condition remotely, or to acquire visual physiological measurements of the subject, etc.). In some embodiments, a communication channel provided by the health monitoring device 102 includes the image and or video captured by the optical sensor 368 (e.g., the communication channel includes a video feed or an image).

In some embodiments, the memory 307 of the health monitoring device 102 stores:

an operating system 302 that includes procedures for handling various basic system services;
an electronic address 304 associated with the health monitoring device 102;
a health monitoring application 306 that controls the alarms of the present disclosure;
a candidate subject support member data store 328 that stores information associated with each support member further associated with the subject of the health monitoring device 102;
a GPS driver 330 that provides a current location of the health monitoring device 102;
an audio driver 332 that provides audible sounds through the health monitoring device 102; and
an imaging module 334 that provides image and video capture capabilities.

As illustrated in FIG. 3, a health monitoring device 102 preferably includes an operating system 302 that includes procedures for handling various basic system services. The operating system 302 (e.g., iOS, ANDROID, DARWIN, RTXC, LINUX, UNIX, OS X, WINDOWS, or an embedded operating system such as VxWorks) includes various software components and or drivers for controlling and managing general system tasks (e.g., memory management, storage device control, power management, etc.) and facilitates communication between various hardware and software components.

An electronic address 304 is associated with each health monitoring device 102 in order to uniquely identify the health monitoring device. In some embodiments, the health monitoring device 102 includes a serial number, and optionally, a model number or manufacturer information that further identifies the health monitoring device.

A component of the health monitoring device 102 is the health monitoring application 306 (e.g., a health monitoring application of FIGS. 5A through 24). In some embodiments, the health monitoring application 306 includes an alarm test module 310 configured to verify a usability of an alarm trigger condition or feature of the health monitoring application. The alarm test module 310 allows a subject associated with the health monitoring device 102 to become familiar with the health monitoring application without a risk of communicating a false alarm to the health monitoring and emergency support system 150 (e.g., a remote monitoring center).

In some embodiments, the health monitoring application 306 includes a system hardware test module 312 configured to verify a usability of a component of the system hardware (e.g., verify a current location of the health monitoring device 102, verify a functionality of an input mechanism 378 of the device, verify one or more values obtained from a sensor of the device, etc.). The system hardware test module 312 allows the subject associated with the health monitoring device 102 to verify a functionality of the hardware of the device since, in some circumstances, a well-being of the subject is dependent on properly functioning hardware.

In some embodiments, the health monitoring application 306 includes an alarm input module 314 (e.g., that allows a subject and/or support member to input an alarm (e.g., input a trigger condition)). In some embodiments, the alarm input module 314 allows for receiving an alarm communicated from a remote device 104 (e.g., the remote device communicates a pre-configured alarm to the health monitoring device 102 for storage on the health monitoring device). For instance, in some embodiments a medical practitioner associated with a subject of a health monitoring device 102 inputs an alarm 208 from a remote device, which is then communicated to the health monitoring device 102 and/or the health monitoring and emergency support system 150. This communication of the alarm allows a medical practitioner to configure various alarms and trigger conditions according to the needs of each respective subject.

In some embodiments, the health monitoring application 306 includes an audio and video capture module 318 allowing the device 102 to capture audio and video imagery through the heath monitoring device 102. This audio and video imagery allows for a communication channel to be opened between a respective health monitoring device 102 and corresponding remote device 104 and/or the health monitoring and emergency support system 150 (e.g., a remote alarm monitoring center). Furthermore, the capturing of audio and video imagery allows for the health monitoring and emergency support system 150, or similarly an emergency responder dispatched by the health monitoring and emergency support system, to receive audio or video imagery from a health monitoring device 102 associated with a fired alarm.

In some embodiments, the health monitoring application 306 includes a user settings module 320 that allows a user to adjust personal settings and information (e.g., field 1810, field 1820, and/or field 1830 of FIG. 18, and field 1910, field 1920, and field 1930 of FIG. 19) within the health monitoring application. In some embodiments, access to the user settings module 320 is in accordance with a determination of an alarm state of the respective device 102. For instance, in some embodiments if an alarm (e.g., the health monitoring device 102 and/or health monitoring application 306) is in an armed state (e.g., in a state illustrated in FIGS. 5A and 5B) an end-user of the health monitoring device 102 is restricted from modifying the user settings 320 (e.g., provided a prompt 1302 of FIG. 13). This restriction prevents the user from, at least, modifying essential information used in an emergency situation while the respective health monitoring device 102 is armed (e.g., in a state ready to communicate an alarm or trigger condition).

Figure 5A:
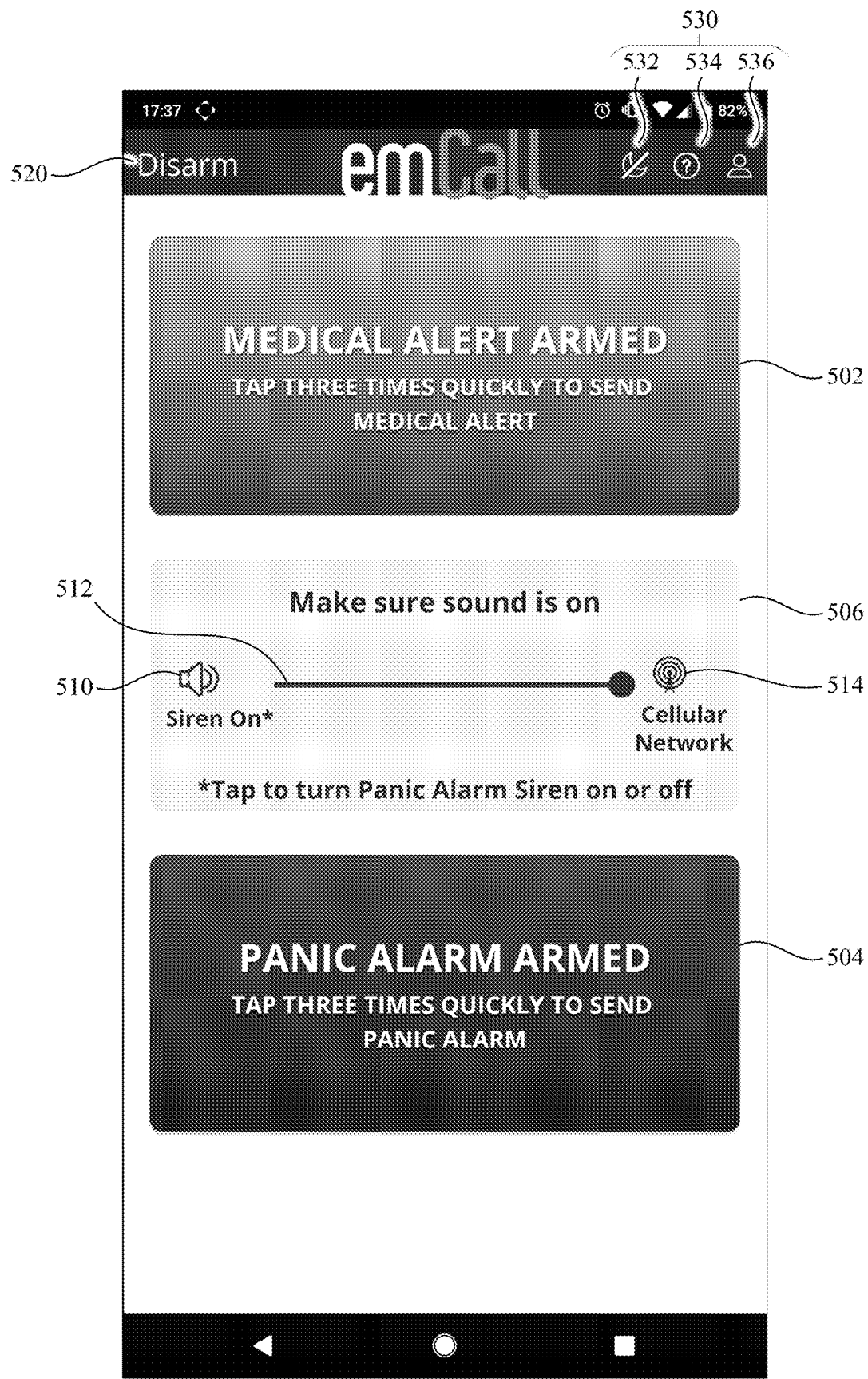
FIGS. 5A and 5B illustrate user interfaces for armed alerts accordance with exemplary embodiments of the present disclosure.

In some embodiments, the health monitoring application 306 includes an application settings module 322 that enables an end-user to adjust the settings of the application (e.g., a volume setting 510 of FIG. 5A for an alarm and/or alert). In some embodiments, the settings of the application settings module 332 include a desired graphical user interface (GUI) of the health monitoring application 306. For instance, in some embodiments the end-user of the health monitoring application 306 configures the application between a plurality of GUIs (e.g., configures the application between a first GUI of FIG. 5A, a second GUI of FIG. 7A, a third GUI of FIG. 8A, a fourth GUI of FIG. 8C, etc.).

Figure 17:
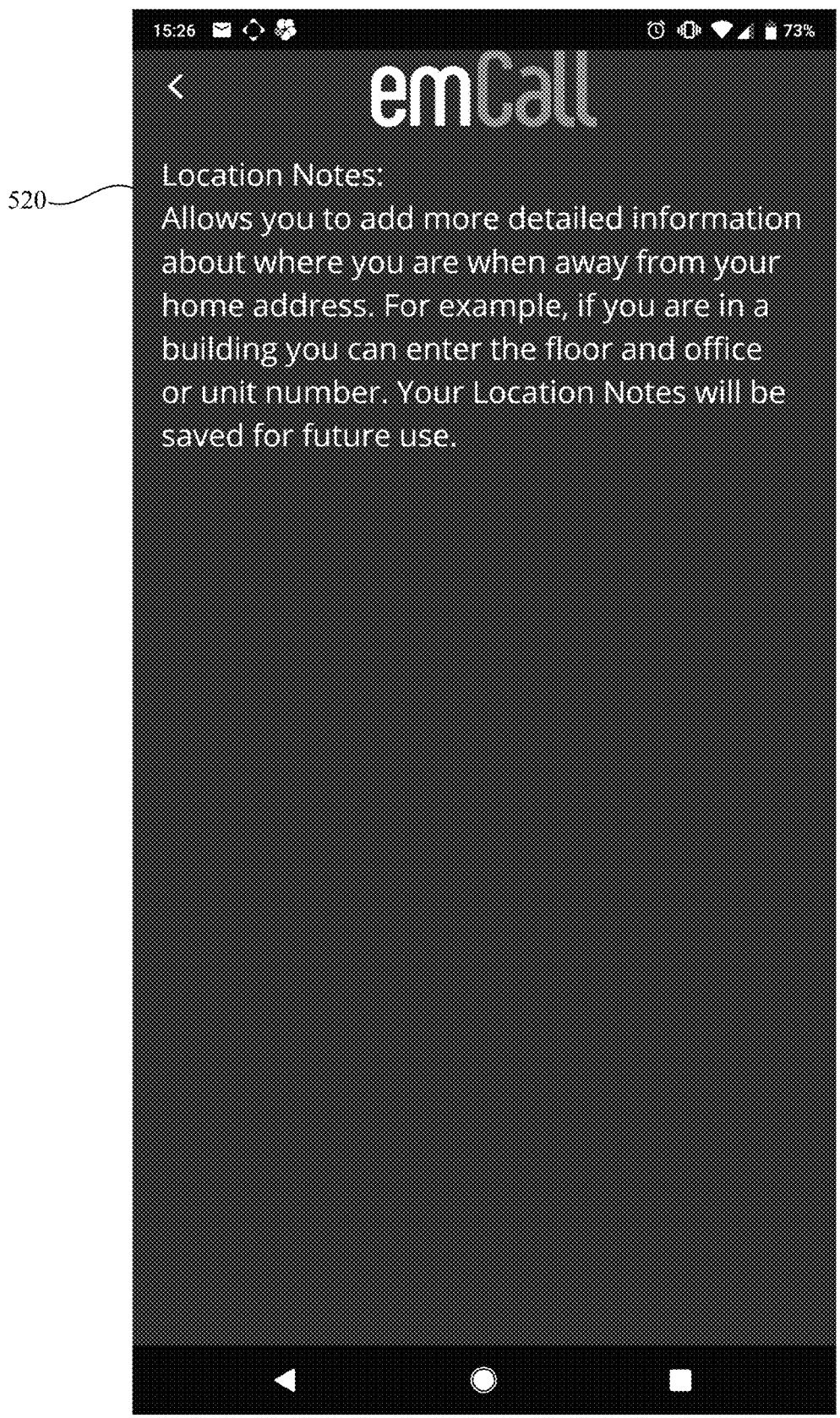
FIG. 17 illustrates a user interface for providing application information in accordance with an exemplary embodiment of the present disclosure.
Figure 18:
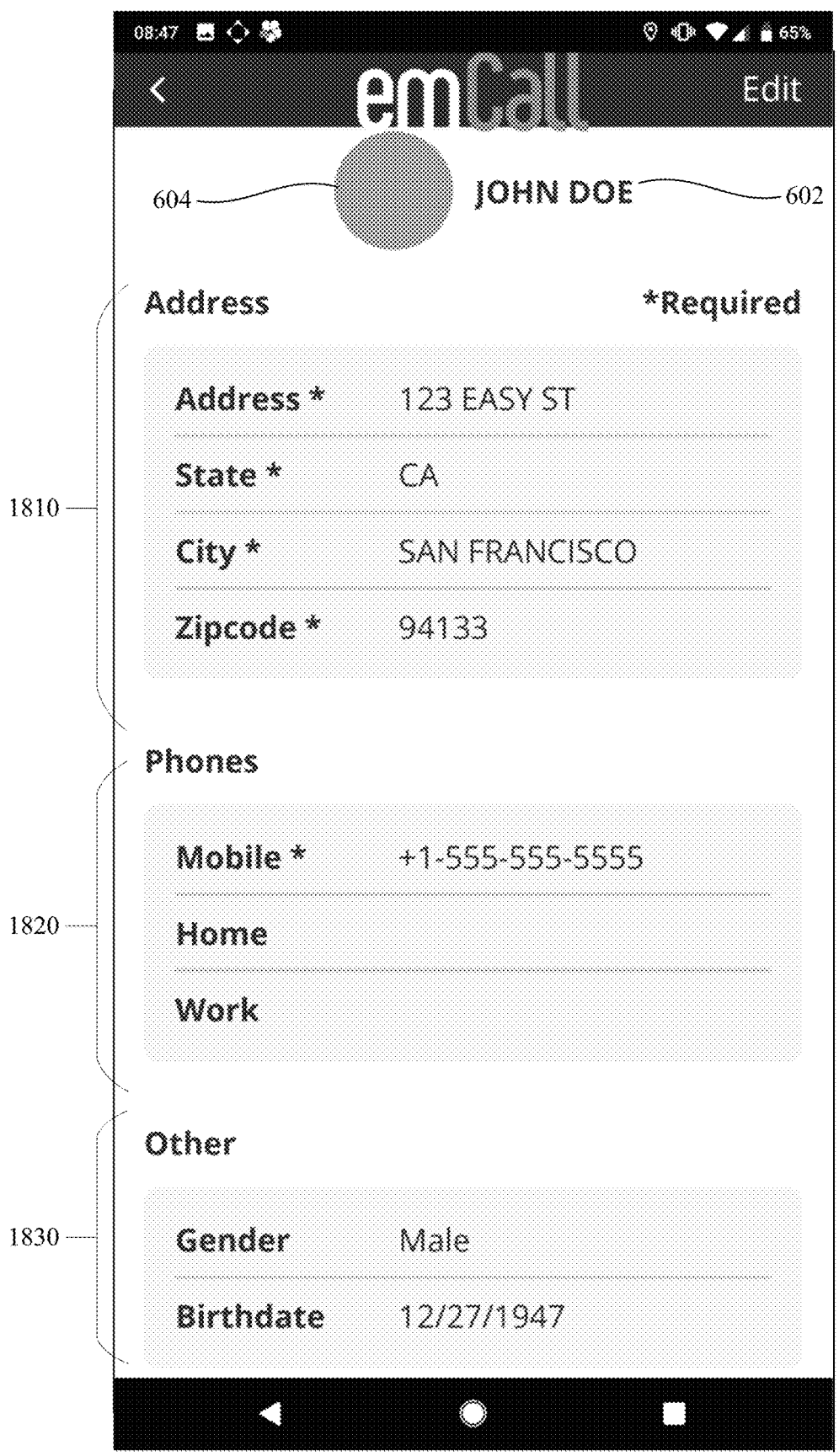
FIG. 18 illustrates a user interface for modifying a user profile in accordance with an exemplary embodiment of the present disclosure.
Figure 19:
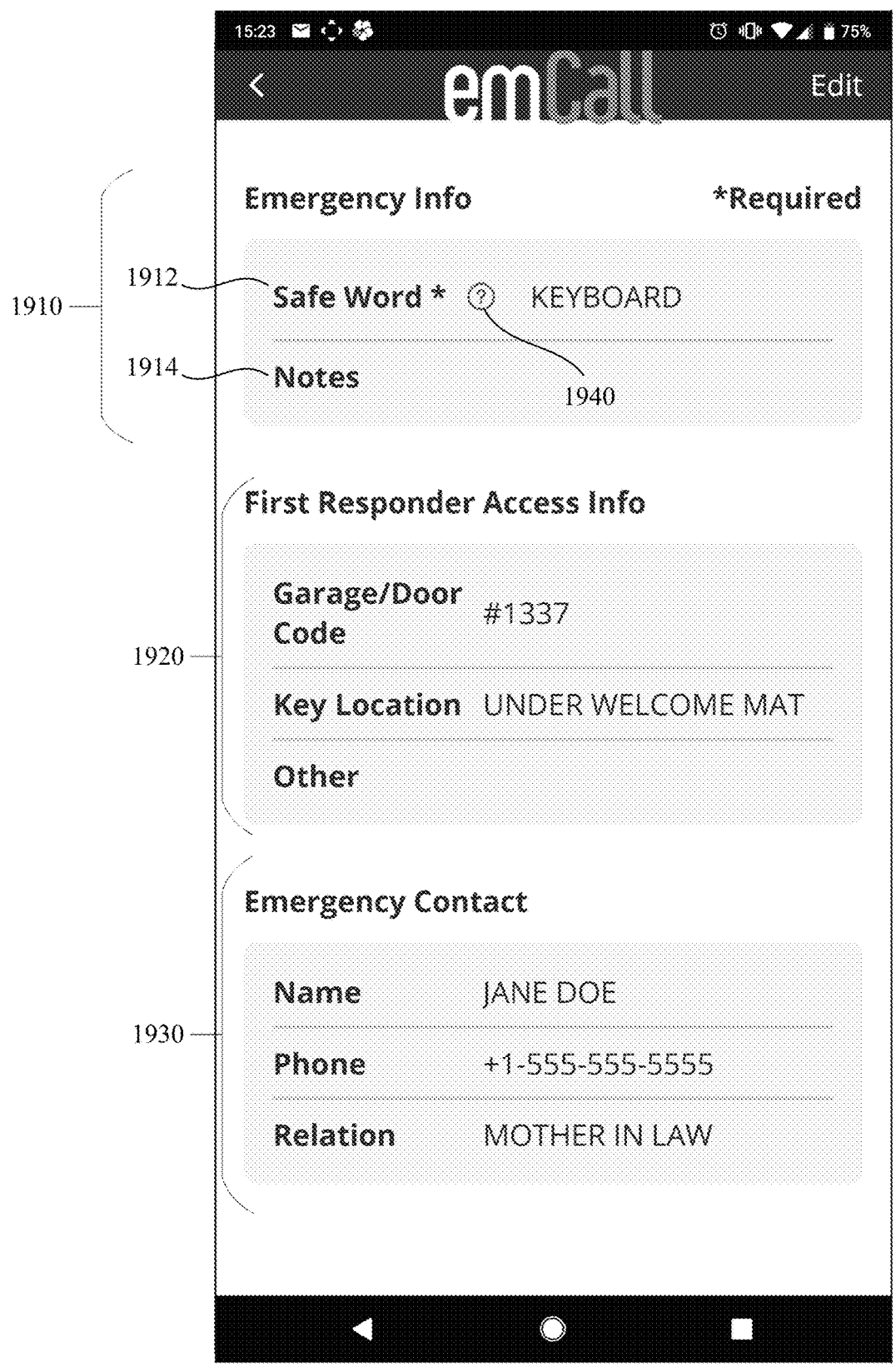
FIG. 19 illustrates a user interface for modifying a user profile in accordance with an exemplary embodiment of the present disclosure.
Figure 20:
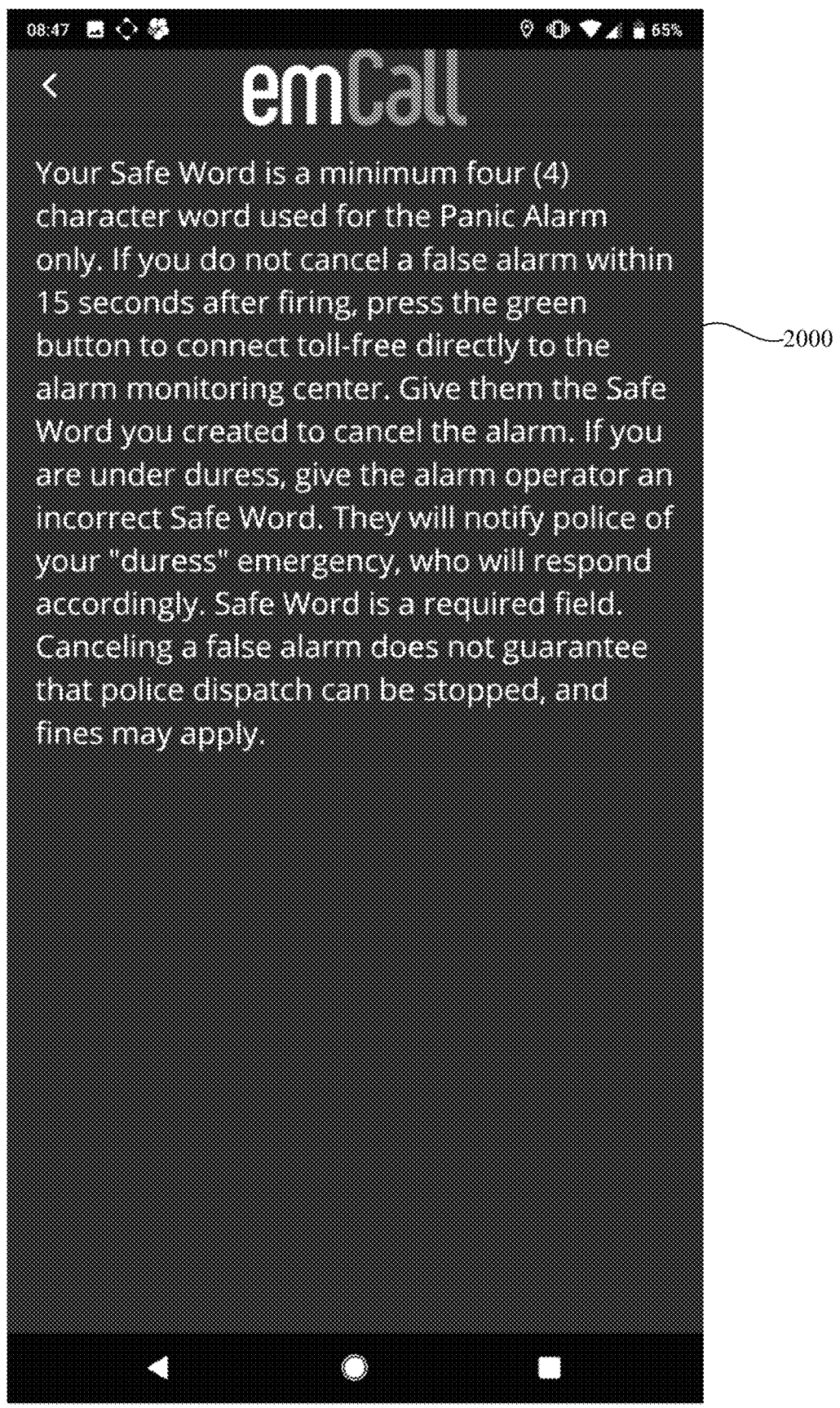
FIG. 20 illustrates a user interface for providing system information in accordance with an exemplary embodiment of the present disclosure.

In some embodiments, the health monitoring application 306 includes a location module 324 that provides a current location of the health monitoring device 102 (e.g., a GPS location of the subject). In some embodiments, the location module 324 allows the subject associated with of the health monitoring device 102 to include personalized notes or comments regarding a current and/or previous location associated with of the subject and/or the device (e.g., note 1610 and/or note 1620 of FIG. 16). Since some GPS systems (e.g., GPS 372 of FIG. 3) do not include a vertical (e.g., elevation) component, a personalized note describing the current location conserves valuable time for an emergency responder to locate the subject during an emergency situation, as illustrated by an instruction 520 of FIG. 17 provided to an end-user of through a user interface of the health monitoring application 306. In some embodiments, the personalized notes are stored for future user, allowing the subject to readily switch between stored personalized notes when changing between common locations (e.g., a first note 1620-1 describing a house of the subject, a second note 1620-2 describing an office of the subject, etc.). In some embodiments, the location module 324 polls for a current location of the health monitoring device on a recurring basis (e.g., every second, every two seconds, every five seconds, every ten seconds, every fifteen seconds, every minute, etc.). In some embodiments, the recurring basis is determined by a triggering of an alarm 208 (e.g., if an alarm is triggered the recurring basis is set to a first value, if an alarm has not been triggered the recurring basis is set to a second value).

Furthermore, in some embodiments the health monitoring application 306 includes an alert module 326 that provides an alarm and/or alert. In some embodiments, the alert module 326 is configured to provide a plurality of alerts that are each associated with a unique trigger condition and/or notification process (e.g., a low tier or low priority alert, a high tier or high priority alarm, etc.). For instance, in some embodiments the alert module 326 includes a medical alert (e.g., medical alarm 502 of FIG. 5) and/or a panic alert (e.g., panic alarm 504 of FIG. 5). Differentiating between different types of alerts and alarms allows for the health monitoring and emergency support system 150 to provide services to the end-user of the respective device that communicates the alarm depending on the situations and conditions that triggered the alarm. For instance, in some embodiments a medical alarm allows for the health monitoring and emergency support system 150 to open a communication channel (e.g., a voice call, a video feed, etc.) with the health monitoring device 102 that communicates the alarm to confirm a need for emergency services. A panic alarm in some embodiments allows for the health monitoring and emergency support system 150 to immediately provide emergency services (e.g., dispatch police). In some embodiments, the alert module 326 provides a silent alarm (e.g., a state of a volume indication 510 of FIG. 5A is in a MUTE state) that communicates a potential criminal situation (e.g., a robbery) to the health monitoring and emergency support system 150. Furthermore, differentiating between different types of alerts and alarms allows for the health monitoring and emergency support system 150 to communicate different information depending on the type of alert or alarm. Since communication of sensitive personal medical information includes an inherent risk of mishandling the information, it is necessary to restrict what information is communicated with a data element 208.

In some embodiments, the health monitoring device 102 includes a candidate subject support member data store 328 that stores various information related to each support member further associated with the subject of the health monitoring device. For instance, referring briefly to FIG. 19, in some embodiments the health monitoring application 306 includes emergency contact information 1930 that provides contact information (e.g., support member contact info 220 of FIG. 2) associated with one or more support members further associated with the subject of the health monitoring device 102. This emergency contact information includes a name of the support member (e.g., Jane Doe), a phone number of the support member, a relationship of the support member to the subject of the health monitoring device (e.g., mother-in-law, sister, unrelated, etc.), an address of the support member (e.g., electronic address 304 of the remote device associated with the support member, an email address of the support member, a street address of the support member, etc.), or a combination thereof (e.g., support member contact information 220 of FIG. 2). Further, in some embodiments the candidate subject support member data store 328 includes a schedule of each support member (e.g., support member schedule 222 of FIG. 2) and/or an alarm type associated with each support member (e.g., support member alarm types 224 of FIG. 2). In some embodiments, the candidate subject support member data store 328 is in communication with (e.g., shares data between) the subject support list 216 of the health monitoring and emergency support system 150.

In some embodiments, the health monitoring device 102 includes a GPS driver 330. The GPS driver 330 utilizes data from the GPS 372 to provide a current location of +the health monitoring device 102. For instance, referring briefly to FIG. 7A, in some embodiments the health monitoring application 306 provides a current location 702 of the health monitoring device. The current location 702 includes one or more GPS coordinates of the health monitoring device 102 (e.g., a latitude and/or a longitude), an elevation of the health monitoring device, a tolerance of the current location 702 (e.g., within a range of ±65 seconds of a provided GPS coordinate), or a combination thereof.

In some embodiments, the health monitoring application 306 includes an audio driver 332 and/or an imaging module 334.

In some embodiments, the health monitoring device 102 has any or all of the circuitry, hardware components, and software components found in the system depicted in FIG. 3. In the interest of brevity and clarity, only a few of the possible components of the health monitoring device 102 are shown to better emphasize the additional software modules that are installed on the health monitoring device.

Figure 4:
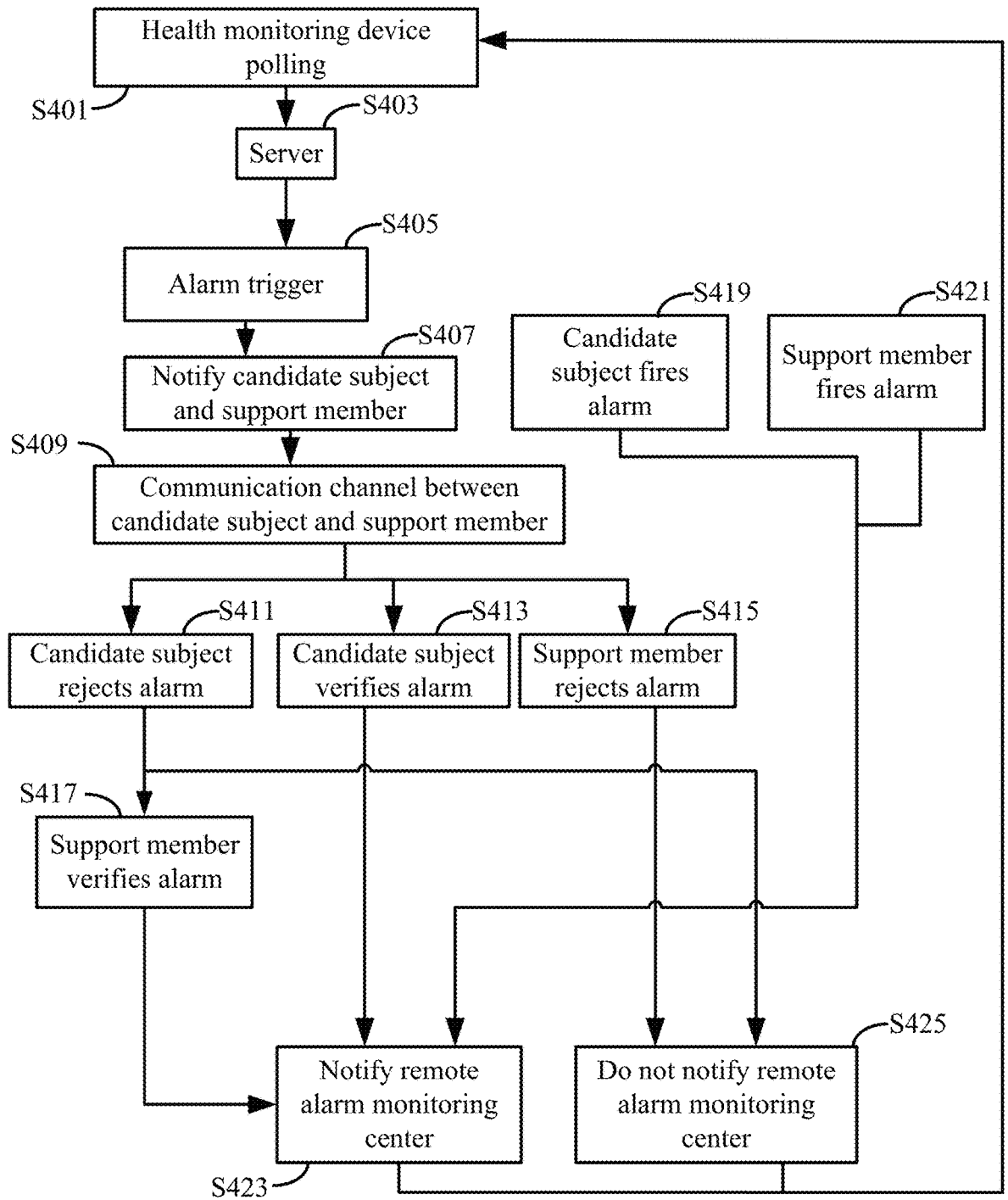
FIG. 4 provides a flow chart of processes and features of a computer system for a health monitoring emergency support system in accordance with an exemplary embodiment of the present disclosure.

Now that details of a system 148 for providing a health monitoring and emergency support system have been disclosed, details regarding a flow chart of processes and features of the system, in accordance with an embodiment of the present disclosure, are disclosed with reference to FIG. 4.

Referring to FIG. 4, a health monitoring device 102-1 from a plurality of health monitoring devices 102 polls for an alert trigger in the form of a respective data element (S401). This polling for a respective data element occurs continuously or on a recurring basis. In some embodiments, the alert trigger condition is a health event such as a detected change in temperature of a subject associated with the health monitoring device 102, a detected change in blood pressure of the subject, a detected heart attack, a detection of a slip or fall (e.g., a sudden chance in data from an accelerometer 397), a distress signal (e.g., detecting a call to police), an irregular heartbeat (e.g., a measurement provided by a pacemaker), or a detected change in blood glucose concentration. As previously described, in some embodiments the alert trigger condition is provided by a medical practitioner in order to tailor each trigger condition to an individual subject. In some embodiments, the health monitoring device 102 includes a diabetes glucose monitor, heart rate monitor, EKG monitor, a wearable device, or the like (e.g., a conductive energy weapon). Accordingly, in some embodiments an alert trigger in the form of a respective data element includes detecting use of an external device in communication with the health monitoring device 102 (e.g., detecting use of a conductive energy weapon, detecting breaking of a seal of a medical device including an epinephrine auto-injector or a defibrillator, etc.).

In some embodiments, when the health monitoring device 102 registers an event or condition that warrants an alert trigger (e.g., a detected glucose value that satisfies a threshold value), a respective data element regarding the alert trigger is forwarded to an auxiliary health data analytics server. In such embodiments, the respective data element includes the alert trigger.

In some such embodiments, the data element 208 includes a current location of the respective health monitoring device 102, such as the GPS location of the subject (e.g., location 702 of FIG. 7), and/or audio or video imagery captured from the health monitoring device 102.

In some embodiments, when the health monitoring device 102 registers an event or condition that warrants an alert trigger, a respective data element regarding the alert trigger is forwarded to an auxiliary health data analytics server. In such embodiments, the auxiliary server (e.g., an auxiliary health data analytics server) analyses the event or the condition to determine if, in fact, an alert should be fired. For instance, in some embodiments, this analysis is performed by comparing the alert or the condition to historical data associated with the subject that has been received from the subject in the past (e.g., data stored in the subject data store 210 of FIG. 2). In some embodiments, a trend analysis is performed on this historical data. In some embodiments, this trend analysis determines an occurrence of a combination of conditions associated with the subject such as a blood pressure above a first predetermined threshold combined with a blood glucose level above a second predetermined threshold. As another example, this trend analysis determines an occurrence of a combination of conditions associated with the subject such as candidate subject inactivity for greater than a predetermined period (as determined by data provided by the accelerometer 397 of the health monitoring device 102 associated with the candidate subject) coupled with a physiological measurement (e.g., s blood pressure value, a blood glucose level, a heart rate, etc.) satisfying a threshold value.

In some embodiments, the respective data element is communicated to a gateway or software development kit (SDK) employed on a computing device for further analysis. In one such embodiment, there are two or more classes of devices associated with a candidate subject. The first class of devices constitutes measurement or data gather devices that measure a biometric or physiological value associated with the candidate subject (e.g., on a recurring basis). These data gathering devices then communicate the data to the second class of device which analyzes the data (e.g., against trends or for the occurrence of a combination of conditions). For instance, such analysis includes inferring a trend in measured values, some predetermined value extrema, or the like. In such embodiments, once the respective data element has been analyzed and an alert trigger condition is verified by the analysis, the data element is forwarded to a central command and control server (S403). Hereinafter, the respective data element may be called an alert trigger for simplicity and ease of understanding.

In some embodiments, the first class of devices (e.g., the measurement devices) and the second class of devices (e.g., the analysis devices) are the same devices. In one such embodiment, the first class of devices constitutes a smart phone that includes an accelerometer (e.g., accelerometer 397 of FIG. 3). The smart phone uses the accelerometer to track a change in the motion of the subject. In some embodiments, an SDK is installed on the smart phone. The SDK analyses the motion data obtained by a health monitoring device 102 to determine trends in the data (e.g., no activity by the subject for longer than 20 minutes in the middle of the day is an alert trigger condition).

Furthermore, in some embodiments the SDK is distributed through a chain of computer systems, not just a single computer system. Thus, in such embodiments a first device (e.g., device 102-1) associated with the subject, or several devices associated with the subject monitor one or more conditions of the subject and send data regarding these one or more conditions to another device for analysis (e.g., for trend discovery, for condition mapping, etc.). In so doing, this analysis device may, in turn, invoke another analysis device in order to determine whether an alert should be fired. In some embodiments, this calling process relies on any number of analysis computers in order to arrive at a final decision on whether to call an alert.

Once a respective data element is known to satisfy an alert trigger condition (or criteria), an alert is triggered (S405). Once an alert is triggered a notification is sent to the health monitoring device 102 associated with the subject and the respective remote device 104 of each member 218 of the subject support list 216 (circle of support) of the subject (S407). In some embodiments, a type of alert triggered is dependent upon the satisfying of the alert trigger condition. For instance, in some embodiments a first type of alert is a medical alert (e.g., medical alert input 502 of FIG. 5A) that includes a first alert trigger condition and a second type of alert is a panic alarm (e.g., panic alarm input 505 of FIG. 5A) that includes a second alert trigger condition different than the first alert trigger condition. Differentiating between different types of alarms enables the remote alarm monitoring center (e.g., the health monitoring and emergency support system 150) to provide specific emergency support dependent on the type of alarm received from a health monitoring device 102. For instance, a first subject requiring medical assistant has different emergency response needs than a second subject requiring police assistant in a criminal situation. The remote alarm monitoring center converse precious time in these situations by knowing what type of alarm, and therefore what type of support to provide, through the notifications of the present disclosure.

In some embodiments, the support members to be notified from the subject support list 216 are elected by the predetermined support member alarm types and or the support members' availability (referring to 222 and 224 of FIG. 2B). For instance, a support member can elect to only receive notifications during predetermined times or for predetermined conditions or a combination of the two. In some embodiments, the notification to the electronic device 102 of the subject includes: a list of the members of the circle of support (subject support list 216) and corresponding phone number links (or other forms of electronic contact such as instant message address, an E-mail address, or some combination of the above, referred to here as contact information 220), instructions on how to fire (activate) the alert when desired, and/or insurance information of the subject. In some embodiments, the notification to the electronic devices of the circle of support (CoS) includes the name of the subject and a description of the emergency healthcare condition, the phone number link (or other electronic communication link such as instant messaging address, E-mail address, etc.) of the subject, a list 216 of the circle of support members and their corresponding phone number links (or other electronic communication link such as instant messaging address, E-mail address, etc.), the names of the medical care specialists and corresponding phone number links of the subject, an alarm monitoring center phone number link, the medical alert account number of the subject, and/or the medical insurance information of the subject.

In some embodiments, after a notification has been sent to the health monitoring device 102 of the subject and the remote devices 102 of the circle of support, a communication channel between the subject and corresponding support member is opened in some embodiments (S409). In some embodiments, the communication channel includes a push-to-talk or open channel audio, text, and/or video channels between the device 102 associated with the candidate subject and the devices 104 associated with the subject support members. In some embodiments, the notify (S407) and the communicating (S409) are performed concurrently. In some embodiments, the communicating (S409) is omitted. In some embodiments, the notifications (S407, S409) include an audible alarm or alert. In some embodiments, the audible alarm or alert is configured to seize the attention of nearby persons. For instance, in some embodiments the audible alarm or alert includes a combination of a first sound (e.g., a first siren) and a second sound (e.g., a second sired). In some embodiments, the first sound and the second sound oscillate at different frequencies and/or variable pitches. In typical embodiments, an emergency service such as 911 is not invoked even when the alert is verified either by the candidate subject or a support member 218. Furthermore, in some embodiments the communication channel is between the subject and the remote alarm monitoring center.

In some embodiments, when the alert trigger notification is sent to the electronic device 102 associated with the subject, the subject has the option to either reject (S411) or verify (S413) the alert trigger. When the candidate subject elects to manually verify the alert trigger, in some embodiments the subject does so through the use of the health monitoring application 306 (e.g., through medical alert input 502 and/or panic alarm input 504 of FIG. 5A). In some such embodiments, the verification includes the user pressing a button (e.g., tapping the medical later input 502 of FIG. 5A) a predetermined number of times, thereby placing then the alert in an armed state, in which the alert is communicated to the remote alarm monitoring center unless otherwise cancelled or rejected. In some such embodiments, the verification includes the user pressing a button for a predetermined length of time and/or a predetermined number of times, which arms and then communicates the alert. In some such embodiments, the verification includes the user entering in a verification code sequence (e.g., a passcode), which arms and then communicates the alert. For instance, referring briefly to FIG. 9A, in some embodiments the user is provided with a prompt 902 to enter a password and the user is provided with a field 904 to enter the password. In a further embodiment, the verification includes the user speaking a voice command (e.g., a safe word such as emergency information 1910 of FIG. 19).

Figure 9A:
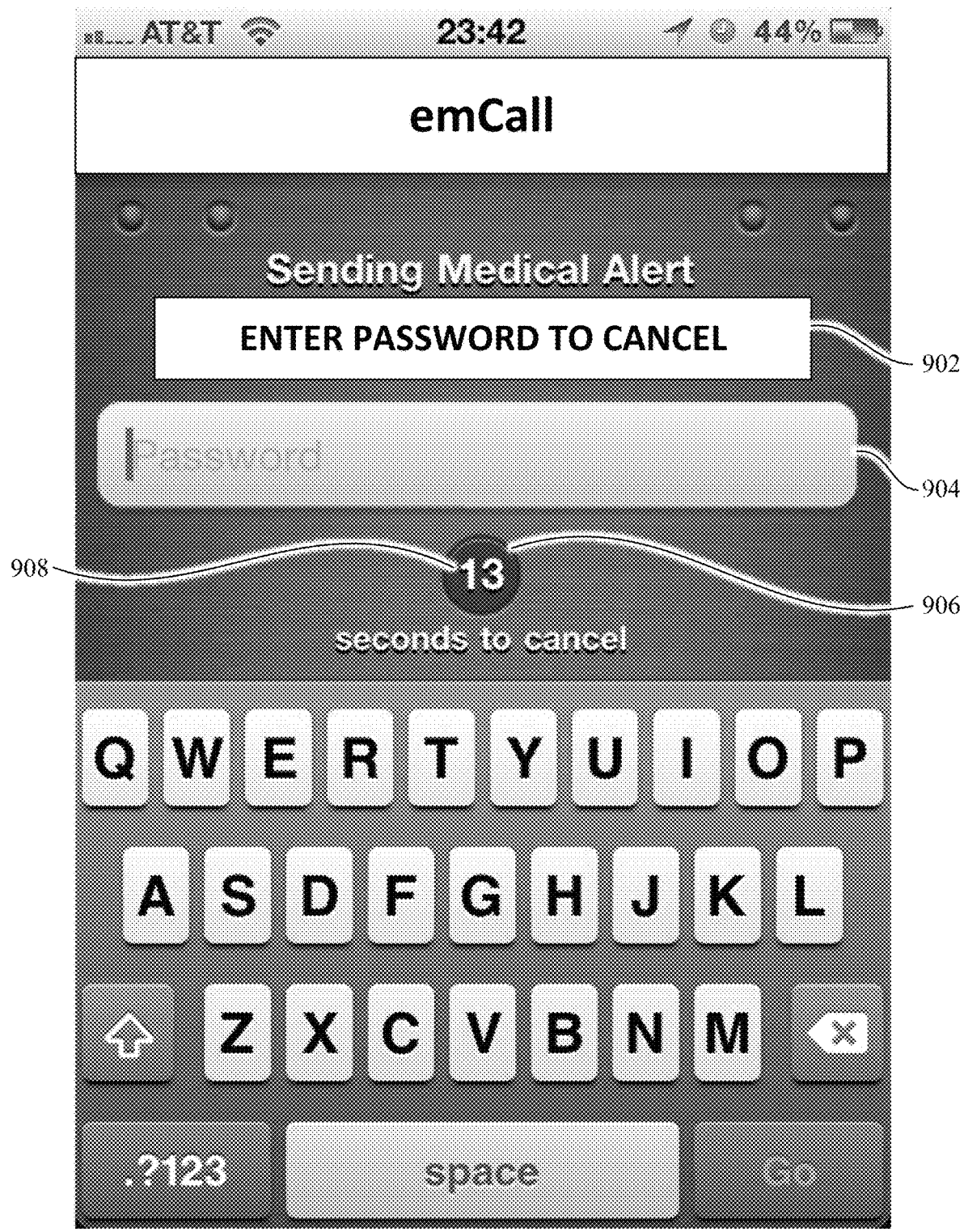
FIGS. 9A, 9B, and 9C illustrate user interfaces for communicating an alarm in accordance with exemplary embodiments of the present disclosure.

In some embodiments, the subject elects to automatically verify every alert trigger and omits manual verification. After an alert is verified, the subject has the option to interrupt or reject the alert (e.g., provided prompt 902 of FIG. 9, provided prompt 1002 of FIG. 10A, etc.). When an alert is interrupted (e.g., the subject provides a password 904 of FIG. 9A, the subject opens a communication channel 1004 of FIG. 10B, etc.), the alert is cancelled and the operations cease for the specific alert. In some embodiments, the subsequent interruption must be received within a predetermined time period of receiving the alert (e.g., within fifteen seconds, within thirty seconds, within a minute, etc.). In some embodiments, the interruption occurs when the user enters a password (e.g., the subject provides a password 904 of FIG. 9A, the subject enters a predetermined personal identification number (PIN), etc.). In some embodiments, the interruption occurs when the user speaks a predetermined safe word (the subject opens a communication channel 1004 of FIG. 10B and provides emergency information 1910 of FIG. 19).

In some embodiments, if the candidate subject verifies an alarm after cancelling an alarm, the verification is treated as a new alarm sequence that the user manually initiated. In such instances, process control passes to S419 and, autonomously without further human intervention, to S423, which is described in further detail below.

Returning to S413, when the candidate subject verifies the alert trigger, the alert is forwarded to an alarm monitoring center (S423). In some embodiments, the remote alarm monitoring center includes a remote alarm company, a physician, a provider group, a hospital, a hospital network, a health insurance company, a pharmacy, a governmental body, a first responder business entity, a prescribing clinician, or a combination thereof. In some embodiments, the forwarding of the alert includes the name of the candidate subject (e.g., name 602 of FIG. 6), a current location of the candidate subject (e.g., a physical street address, GPS coordinates, a location note (e.g., location note 1610 or note 1620 of FIG. 16), etc.), a current phone number of the candidate subject (e.g., subject contact information 214 of FIG. 2), an emergency medical condition reference code associated with the subject and/or a reference code pertaining to a medical condition (e.g., a SNOMED clinical term code), a list of current medications taken by the candidate subject (e.g., medications 2112 of FIG. 21), allergies of the candidate subject (e.g., allergies 2116 of FIG. 21), a name (e.g., name 2132 of FIG. 21) and/or contact information (e.g., information 2134 and/or information 2136 of FIG. 21) of a doctor of the candidate subject, details of emergency contact persons (e.g., the circle of support) for the candidate subject (e.g., emergency contact information 1930 of FIG. 19) and/or photographs of the candidate subject (e.g., image 604 of FIG. 6, an image obtained from image module 334 of FIG. 3, etc.), and/or any combination of the forgoing in addition to other information. In some embodiments, and in accordance with United States protocol, the alarm monitoring center (e.g., health monitoring and emergency support system 150) calls the subject to verify the emergency (e.g., a communication channel between the alarm monitoring center and the health monitoring device 102 associated with the subject is provided). An unanswered call is considered a confirmation of an emergency. In some embodiments, in accordance with a determination that the emergency is confirmed (e.g., by calling the candidate subject, candidate subject verification (e.g., S413 or S419 of FIG. 4), support member verification (e.g., S417 or S421 of FIG. 4), etc.) the alarm monitoring center (e.g., health monitoring and emergency support system 150) dispatches an emergency responder (e.g., a police officer, an emergency medical technician (EMT), a firefighter, etc.) to the subject's geolocation (e.g., current location 702 of FIG. 7) and/or current address (e.g., note 1620 of FIG. 16) provided by the subject and/or the health monitoring device 102 associated with the subject.

In dispatching the emergency responder, in some embodiments a notification is communicated to the emergency responder by the remote alarm monitoring center. This notification to the emergency responder includes the subject's medical information (e.g., medical information 2110 of FIG. 21 such as a time of a latest medical information update 2111, a list of current medications 2112, a list of current health conditions 2114, a list of allergies 2116, a list of associated external devices 2118, a list of auxiliary information 2120, or a combination thereof) and/or the trigger condition of the alarm. In some embodiments, the notification to the emergency responder includes a location note or instruction (e.g., note 1620 of FIG. 16) provided by the subject through the health monitoring application (e.g., health monitoring application 306 of FIG. 3). These location notes 1620 enable the emergency responder to precisely locate the candidate subject if a current location provided by the health monitoring device (e.g., provided by GPS driver 332 of FIG. 3) is insufficient to locate the subject, such as a lack of an evaluation coordinate (e.g., floor level). In some embodiments, the notification to the emergency responder includes access information (e.g., first responder access information 1920 of FIG. 19) that provide instructions for the emergency dispatch to access the current location of the subject (e.g., a garage, door or gate code; a location of a key; etc.).

In some embodiments, when the subject rejects the alert trigger (S411), the remote alarm monitoring center (e.g., health monitoring and emergency support system 150) is not notified (S425). However, in some embodiments when a support member verifies the alert after the subject has rejected the alert, the support member's verification takes precedence (S417). The support member verification (S417) is then forwarded to the alarm monitoring center and the above operations (S423) occur. When more than one support member is asked to verify the alert, precedence is take in order of receipt (e.g., each subsequent response received overrides a previously received response). For instance, when a first support member rejects an alert and a subsequent second support member verifies the alert, the subsequent command takes precedent and is forwarded to the remote monitoring center (S423). Likewise, when a first support member verifies an alert and a subsequent second support member rejects the alert, the subsequent command takes precedent and the remote monitoring center is not notified (S425). In some embodiments, the support member elects to automatically verify any alert triggers. In some embodiments, the support member is notified of the alarm but is not provided the option to reject or verify the alarm (e.g., the candidate subject fires the alarm at S419 and the remote alarm monitoring center is notified at S423).

The support member has the option to reject the alert at his or her discrepancy (S415). For instance, when the support member suspects the subject has fired a false positive alert the support member can reject the alert. Accordingly, the remote alarm monitoring center is not notified (S425). This allows the support member to participate in care giving for the subject while also preventing a false alarm from being communicated to the health monitoring and emergency support system 150, which converses the resources and time of the emergency responders. In some embodiments, the support member is provided a period of time to reject or verify the alert (e.g., provided thirty seconds, provided a minute, provided two minutes, etc.), ensuring the support member does not consume excess time in determining authenticity of the alert.

At any point in time, the subject can fire an alert directly to the remote alarm monitoring center (S419). At any point in time, the subject's support member(s) can fire an alert directly to the remote alarm monitoring center (S421) (e.g., fire an alert from a remote device 104). For instance, in some embodiments the health monitoring device 102 is in communication with an external device (e.g., a conductive energy weapon) and the subject can fire an alert directly to the remote alarm monitoring center by using the conductive energy weapon (e.g., a detected use though communication from the conductive energy weapon to the health monitoring device).

In some embodiments, after the remote alarm monitoring center is or is not notified, the process is reinitiated beginning at S401. In some embodiments, after the remote alarm monitoring center is notified data continues to be extrapolated from the health monitoring device 102. In some embodiments, after the remote alarm monitoring center is notified, audio and/or video imagery is captured from the health monitoring device 102 associated with the subject captured (e.g., captured through the audio driver 332 and/or the imaging module 334 of FIG. 3). In some embodiments, after the remote alarm monitoring center is notified, the health monitoring device polling (S401) and subsequent steps are continuous carried out. In some embodiments, after the remote alarm monitoring center is notified, the subject's geo-location (e.g., current location 702 of FIG. 7) is provided (e.g., notified) to the remote alarm monitoring center on a recurring basis. In some embodiments, the recurring basis is in a range of from 0.1 seconds to 5 seconds, 1 second to 10 seconds, 2 seconds to 10 seconds, 5 seconds to 15 seconds, 5 seconds to 30 seconds, 5 seconds to 60 seconds, 10 seconds to 60 seconds, 10 seconds to 120 seconds, or a similar range of time.

In some embodiments, the health monitoring device 102 can be remotely controlled to capture audio, video, or the like (e.g., open a communication channel between the health monitoring device 102 and the health monitoring and emergency support system 150). For instance, in some embodiments the remote alarm monitoring center (e.g., health monitoring and emergency support system 150) communicates a command to the health monitoring device 102 to capture audio, video, or the like. This allows the remote alarm monitoring center to receive data from the health monitoring device 102 even if the subject is currently incapacitated.

Referring to FIG. 5A through FIG. 24, a graphical user interface (GUI) of a health monitoring application (e.g., health monitoring application 306 of FIG. 3) in an armed state is shown according to an exemplary embodiment of the present disclosure. The GUIs in these figures are used to illustrate the processes described throughout the present disclosure. Although some of the examples which follow will be given with reference to inputs on a touch-screen display (e.g., where the touch-sensitive surface (e.g., input 378 of FIG. 3) and the display (e.g., input 376 of FIG. 3) are combined, for example on health monitoring device 102), in some embodiments the health monitoring device 102 detects inputs on a touch-sensitive surface that is separate from the display (e.g., inputs on a track pad of a laptop computer). For convenience of explanation, the embodiments described with reference to FIG. 5A through FIG. 24 will be discussed with reference to operations performed on a device with a touch-sensitive display system and/or touch screen. For sake of clarity, FIG. 5A through FIG. 24 simply show the touch screen of the health monitoring device 102 without showing other details of the health monitoring device. The GUIs in FIG. 5A through FIG. 24 include the following elements, or a subset or superset thereof: signal strength indicator(s) for wireless communications, such as cellular and Wi-Fi signals; time; a Bluetooth indicator; and a battery status indicator. These well-known elements are not described in detail so as not to unnecessarily obscure aspects of the disclosed embodiments.

Figure 5B:
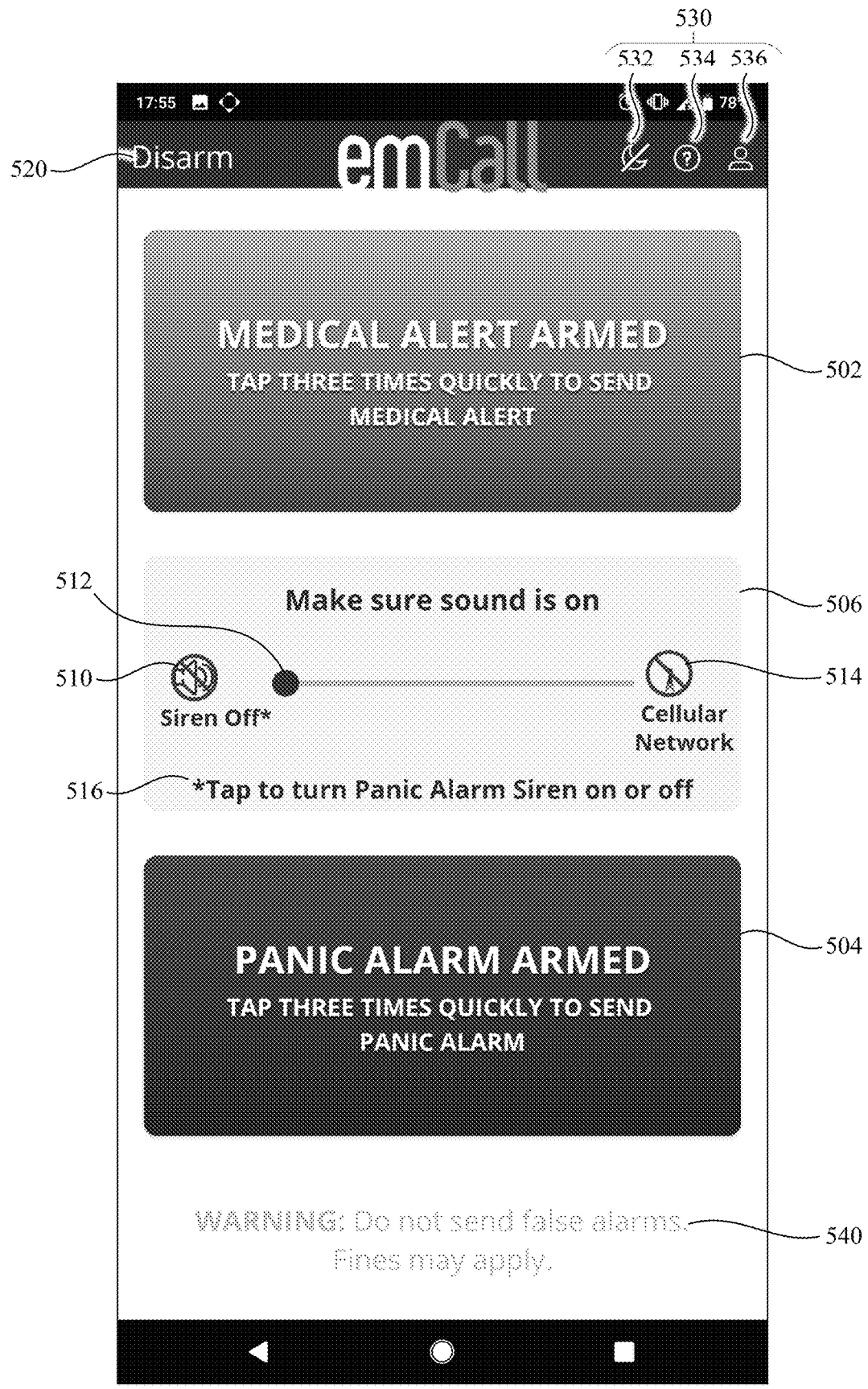

FIGS. 5A and 5B illustrate a GUI of a health monitoring application (e.g., health monitoring application 306 of FIG. 3) in accordance with an embodiment of the present disclosure. The GUI is in an armed state, in which either a medical alert or a panic alarm can be fired (e.g., communicated to the health monitoring and emergency support system 150) in accordance with an input (e.g., tap thrice) from the subject associated with the health monitoring device currently running the health monitoring application. In accordance with a determination that the health monitoring application 306 is provided (e.g., installed) on the health monitoring device 102, the health monitoring application 306 (e.g., a medical alert input 502 and/or a panic alarm input 504) is armed by launching the health monitoring application, which provides the GUI's of, for instance, FIG. 5A or 5B. This arming by launching removes unnecessary steps (e.g., entering a password), which conserves precious time in an emergency situation. Accordingly, once the health monitoring application is launched, an alarm or alert is fired (e.g., S405, S419, and/or S421 of FIG. 4) through a medical alert input 502 and/or a panic alarm input 504.

Figure 8A:
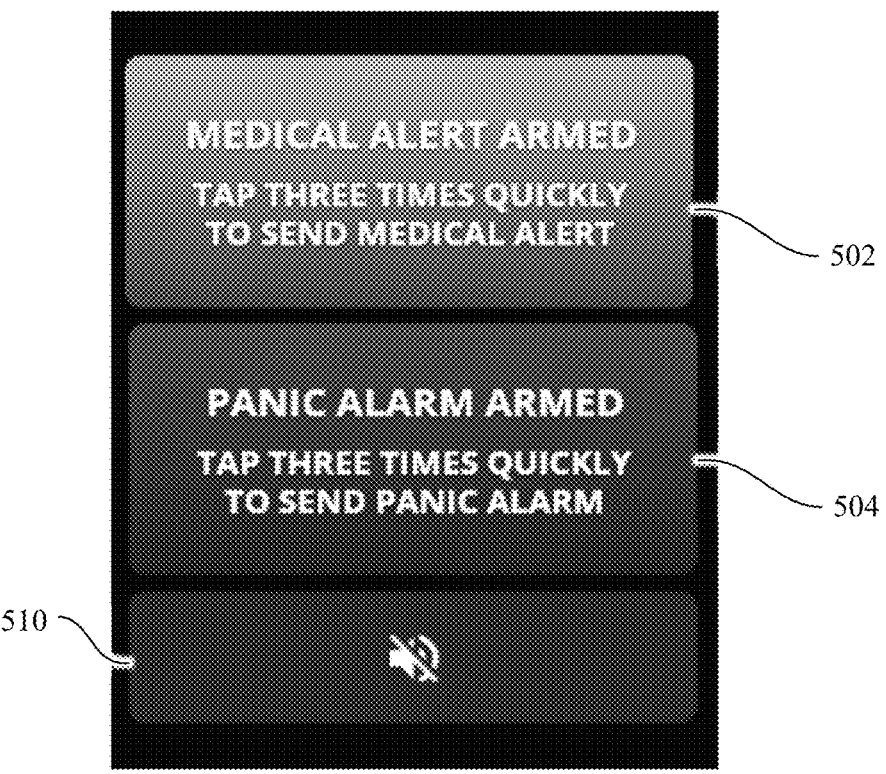
FIGS. 8A, 8B, 8C, and 8D illustrate user interfaces for armed alerts according to an exemplary embodiment of the present disclosure.
Figure 8B:
Figure 8C:
Figure 8D:
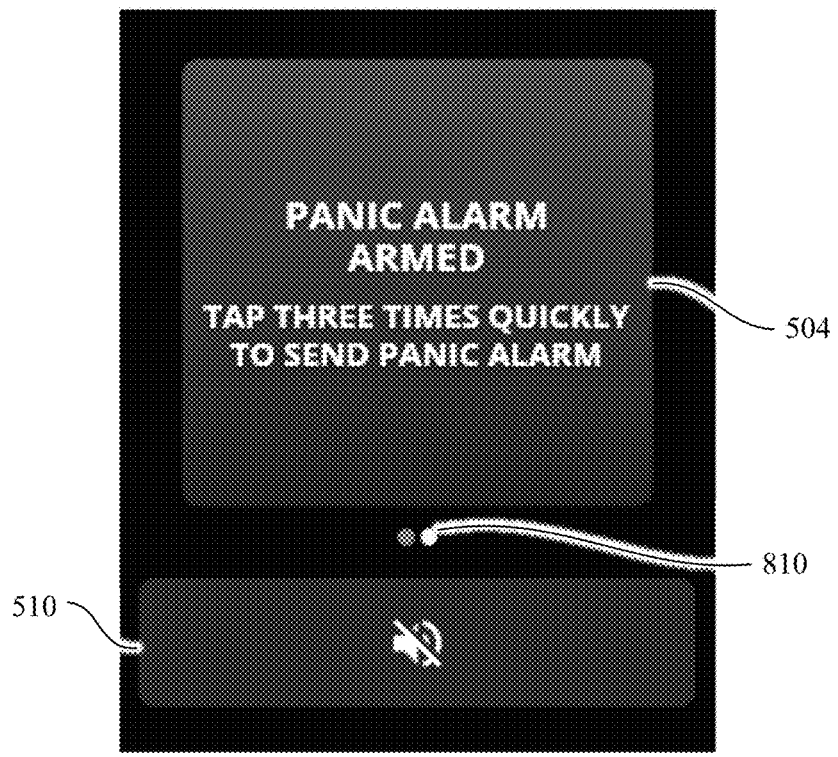

Accordingly, the GUI provides a first affordance region 502 for firing (e.g., inputting) a medical alert (e.g., a medical alert input 502) and a second affordance region 504 for firing a panic alarm (e.g., a panic alarm input 504). In some embodiments, the medical alert input 502 and the panic alarm input 504 have the same shape (e.g., the same height and length as illustrated in FIG. 5A) or have dissimilar shapes (e.g., as illustrated in FIGS. 8A and 8B). Furthermore, in some embodiments the medical alert input 502 and the panic alarm input 504 are colored differently. This difference in color allows an end-user to quickly differentiate between the medial alert input 502 and the panic alarm input 504 in an emergency situation without having to read the text inscribed in the respective inputs. The same is true for embodiments in which the shape of the inputs 502 and 504 are different. Referring briefly to FIG. 8B, in some embodiments the shape of then inputs 502 and/or 504 change upon detection of an interaction by an end-user of the health monitoring application (e.g., the interaction enlarges a shape of an input, the interaction shrinks a shape of an input, etc.).

In some embodiments, the GUI includes a third affordance region 506 for configuring one or more settings of the health monitoring application. For instance, in some embodiments the GUI includes a volume indicator 510 providing a status of a volume setting of the health monitoring application and/or the health monitoring device 102 running the health monitoring application, a volume slider 512 for controlling the volume setting of the health monitoring application and/or the health monitoring device running the health monitoring application, and a network signal strength indicator 514 of the health monitoring application and/or the health monitoring device 102 running the health monitoring application. In some embodiments, the volume indicator 510 and/or the network signal strength indicator 514 are intractable in order to quickly configure the respective setting (e.g., configure a volume setting from ON to MUTE, configuration a network status from ON to OFF, etc.). For instance, in some embodiments the GUI provides an instruction for operating the volume indicator 510 and/or the network signal strength indicator 514 (e.g., instruction 516 to tap the volume indicator 510 to turn a siren ON or OFF). Furthermore, in some embodiments the volume indicator 510 and/or the network signal strength indicator 514 change graphical appearance in accordance with a state of the respective setting (e.g., the indicator includes a general prohibition sign if in an OFF or MUTE state). This change in graphical appearance allows an end-user of the health monitoring application to quickly determine a state of each indicator during an emergency situation.

In some embodiments, a data element communicated from a health monitoring device 102 running the health monitoring application 306 includes information describing a state of the volume indicator 510. For instance, in some embodiments if the volume indicator is in a MUTE state, a data element communicated from the health monitoring device 102 includes information describing that the health monitoring device is in the MUTE state (e.g., an indication of a silent panic alarm). This scenario is particularly useful if the emergency situation includes criminal activity and a subject does not want to draw attention to themselves in firing an alarm. Accordingly, the remote monitoring center (e.g., the health monitoring and emergency support system 150) determines that the silent panic alarm is triggered and notifies emergency responders. This allows the emergency responders to know that the subject is in a potentially criminal emergency situation and provide an appropriate response. In some embodiments, the listing of medical information is provided on the GUI after a predetermined period of time has elapsed since the alarm was fired. In some embodiments, the predetermined period of time to provide the listing of medical information is in a range of from 10 seconds to 240 seconds, 10 seconds to 180 seconds, 15 seconds to 120 seconds, 15 seconds to 90 seconds, 15 seconds to 60 seconds, 30 seconds to 60 seconds, 30 seconds to 45 seconds, or a similar period of time (e.g., a range of time configurable through the application settings module 322 of FIG. 3).

In some embodiments, one or more audio files are coupled with a state of the network signal strength indicator 514. For instance, in some embodiments, if the state of the network signal strength indicator 514 changes (e.g., from ON to OFF, etc.) an audio file is played through the health monitoring device 102 (e.g., via audio driver 332 of FIG. 3). In such embodiments, the audio file provides an announcement that the network (e.g., network 106 of FIG. 1) is unavailable and no alarm is available (e.g., the remote alarm monitoring center will not be notified of the alarm due to a lack of network availability), or similarly, that the network is available and alarms are available. In some embodiments, if the network 106 is unavailable when an alarm is fired, the alarm is communicated to the remote alarm monitoring center once the network 106 is available.

In some embodiments, the GUI includes a third affordance region 520 that is configured to place the health monitoring application in a disarmed state (e.g., disarm the medical alert 502 and/or the panic alarm 504 such that the polling of S401 of FIG. 4 does not occur).

In some embodiments, the GUI provides a fourth affordance region 530 for providing application information related to the health monitoring application and navigating the GUI. In some embodiments, the application information 530 includes a display configuration button 532, a help menu button 534, a user profile configuration button 536, or a combination thereof.

Figure 12:
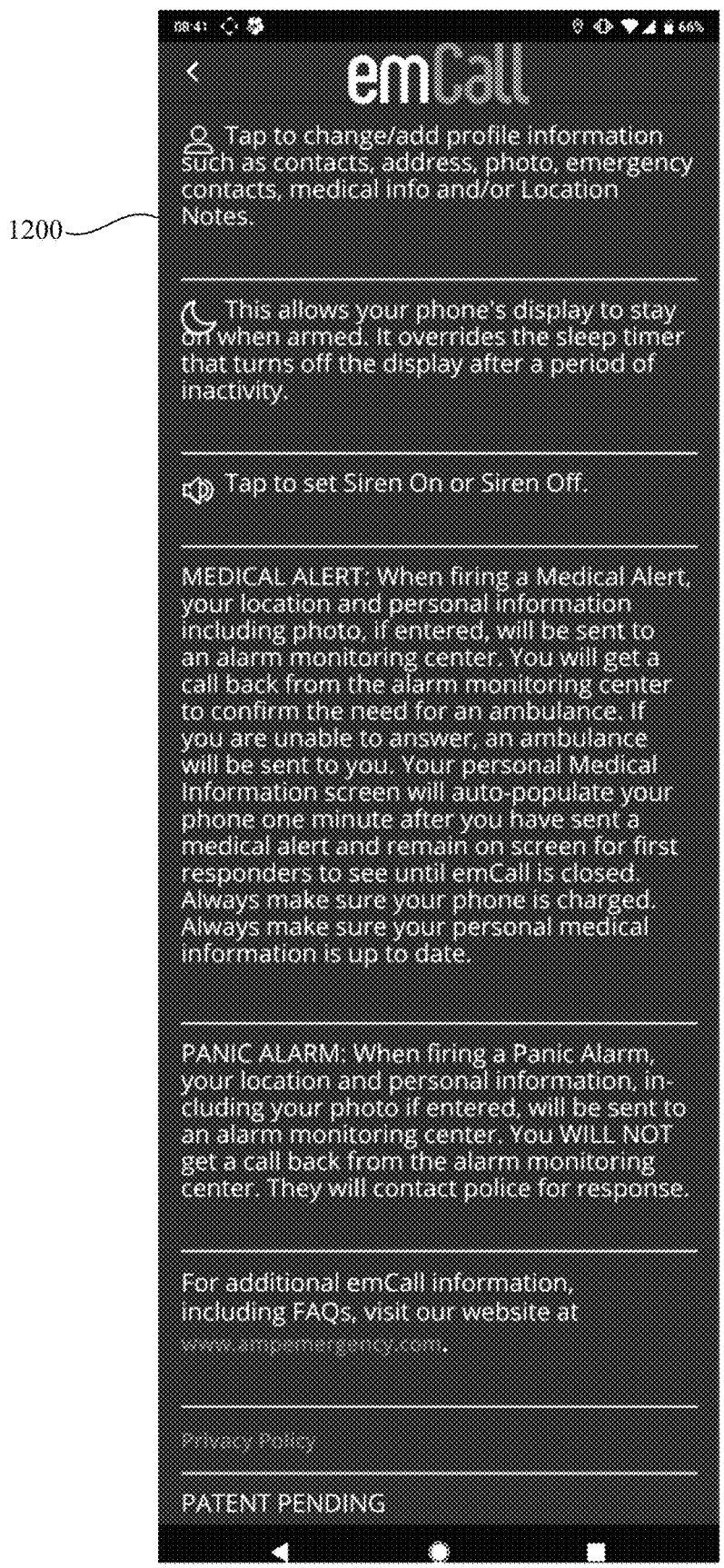
FIG. 12 illustrates a user interface for providing application information in accordance with an exemplary embodiment of the present disclosure.

Referring briefly to FIG. 12, in some embodiments in accordance with a determination that an end-user of the health monitoring device 102 interacts with (e.g., taps) the help menu button 534, the health monitoring application navigates to an information page 1200. The information page 1200 illustrated in FIG. 12 includes instructions for changing or adding profile information, overriding a display setting of the health monitoring device 102, changing a volume setting, or providing further information related to the health monitoring application (e.g., a listing of frequently asked questions, a link to a third-party website, etc.). However, the present disclosure is not limited thereto as one skilled in the art will know of other pertinent information that can be included in the information page 1200.

In some embodiments, a link to the third-party website is included in notifying the remote alarm monitoring center 150 and/or the remote devices 104 associated with the health monitoring device 102. This link allows the remote alarm monitoring center 150 and/or the remote devices 104 to view the information (e.g., a listing of medical information associated with the candidate subject) without having access to the health monitoring device 102. Furthermore, this links in some embodiments is communicated to emergency dispatch responders that are responding to the alarm and/or traveling to a current location of the health monitoring device 102. In some embodiments, the notifying includes a password associated with the link, which is required to access the third-party website. Furthermore, in some embodiments the link to the third-party website is available (e.g., directs to the third-party website) for a predetermined period of time. In some embodiments, the predetermined period of time is in a range of from 1 minute (min) to 60 min, from 5 min to 60 min, from 5 min to 120 min, from 10 min to 180 minutes, or from 30 minutes to a day. This password and/or predetermined period of time prevents access to the subject's medical information outside of the instantaneous emergency situation.

Referring back to FIG. 5B, in some embodiments the GUI includes a first warning 540. Since the present disclosure relates to providing emergency response services, in some geographical regions fees and/or fines are associated with dispatching emergency responders. Since the end-user is ultimately responsible for these fees and/or fines, it is advantageous to warn the end-user of any possible fines related to firing an alarm or an alert. In some embodiments, the warning 540 transitions (e.g., flashes or pulses) between a first state and a second state (e.g., an invisible state as illustrated in FIG. 5A and a visible state as illustrated in FIG. 5B) to capture the attention of the end-user.

While the GUI of FIGS. 5A and 5B illustrates the medical alert input 502 and the panic alarm input 504 on a same screen the present disclosure is not limited thereto. For instance, referring briefly to FIGS. 7A, 7B, 8C, and 8D various GUI's of a health monitoring application in an armed state are illustrated in which only one of the medical alert input 502 (e.g., FIGS. 7B and 8C) or the panic alarm input 504 (e.g., FIGS. 7A and 8D) is displayed. Having only one of the medical alert input 502 or the panic alarm input 504 displayed on a GUI prevents false firing of the other type of alert/alarm that is not being displayed. In some embodiments, the GUIs of FIGS. 8A through 8D are utilized by a health monitoring device 102 configured as a wearable device (e.g., a smart watch). These GUIs are compact and devoid of optional and/or non-essential components since a display (e.g., display 374 of FIG. 3) have smaller resolution than other types of devices (e.g., a smart phone type health monitoring device 102).

Figure 6:
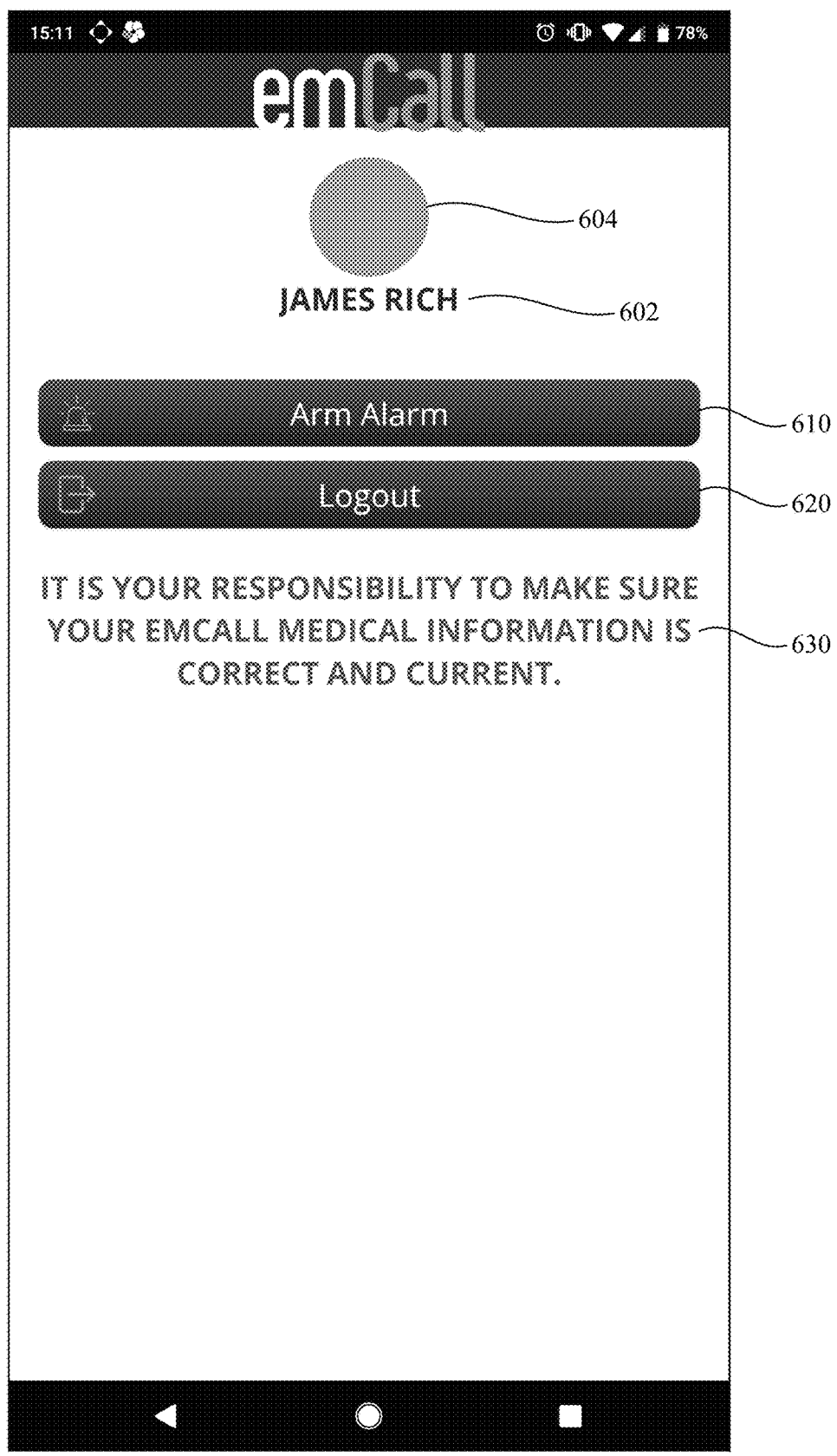
FIG. 6 illustrates a user interface for disarmed alerts according to an exemplary embodiment of the present disclosure.

Referring to FIG. 6, a GUI of a health monitoring application in a disarmed state is illustrated. If the health monitoring application is in the disarmed state (e.g., the polling of S401 of FIG. 4 ceases), alarms and/or alerts cannot be communicated to the remote alarm monitoring center (e.g., the health monitoring and emergency support system 150) until the health monitoring application is placed in an armed state (e.g., an end-user interactions with an arm alarm input 610, the polling of S401 commences, etc.). In some embodiments, the GUI of the disarmed state includes one or more portions of the subject contact information (e.g., subject contact information 214 of FIG. 2B), such as a name 602 and an image 604 associated with the end-user. In some embodiments, the GUI of the disarmed state includes a logout input 620 that allows an end-user of the health monitoring application to logout of a first profile and, for instance, log in to a second profile that is unassociated with the first profile (e.g., log in to a second subject profile 212-2). Furthermore, in some embodiments the GUI of the disarmed state includes a second warning 630. This second warning captures the attention of the end-user and ensure that their personal information is correct which allows emergency dispatchers to provide the correct care to the subject. In some embodiments, requiring an end-user (e.g., subject) to provide a password and/or additional information (e.g., login information 2320 of FIG. 23 such as an email address) protects the personal information (e.g., fields 1810, 1820, and 1830 of FIG. 18) and/or the medical information (e.g., medical information 2110 and/or 2130 of FIG. 21) from unauthorized access.

Figure 7A:
FIGS. 7A and 7B illustrate user interfaces for a panic alarm and medical alert, respectively, according to an exemplary embodiment of the present disclosure.

FIG. 7A illustrates a GUI of a panic alarm 504 when sent to the electronic devices of the subject and support members (e.g., health monitoring device 102 and/or remote device 104). A panic alarm is typically an alarm that is manually fired by the subject. In the embodiment illustrated in FIG. 7A, the end-user must press (e.g., tap) the panic alarm input 504 three times to send the alarm (e.g., commutate the alarm to the remote monitoring center). However, the present disclosure is not limited thereto. For instance, in some embodiments the user must press the panic alarm input 504 more than a predetermined number of times (e.g., three times) or in a predetermined sequence (e.g., consecutive inputs in a predetermined period of time such as three inputs within four seconds). As shown in FIG. 7A, the GUI includes information including a current location 702 of the health monitoring device, a network signal strength indicator 514, alert or alarm volume slider 512, and/or an alert or alarm volume indicator 510. However, the present disclosure is not limited thereto. For instance, in some embodiments, the information includes an emergency responder's estimated arrival time (ETA), an elapsed time since triggering the panic alarm, or the like. In some embodiments, the GUI includes a listing of medical information (e.g., medical information 2110 or medical information 2130 of FIG. 21). This listing of medical information allows an emergency responder to have access to the subject's medical information when at the current location of the health monitoring device 102 without having to configure (e.g., unlock) the health monitoring device 102. This listing is particularly useful if the subject is incapacitated and unable to communicate with an emergency responder.

Figure 21:
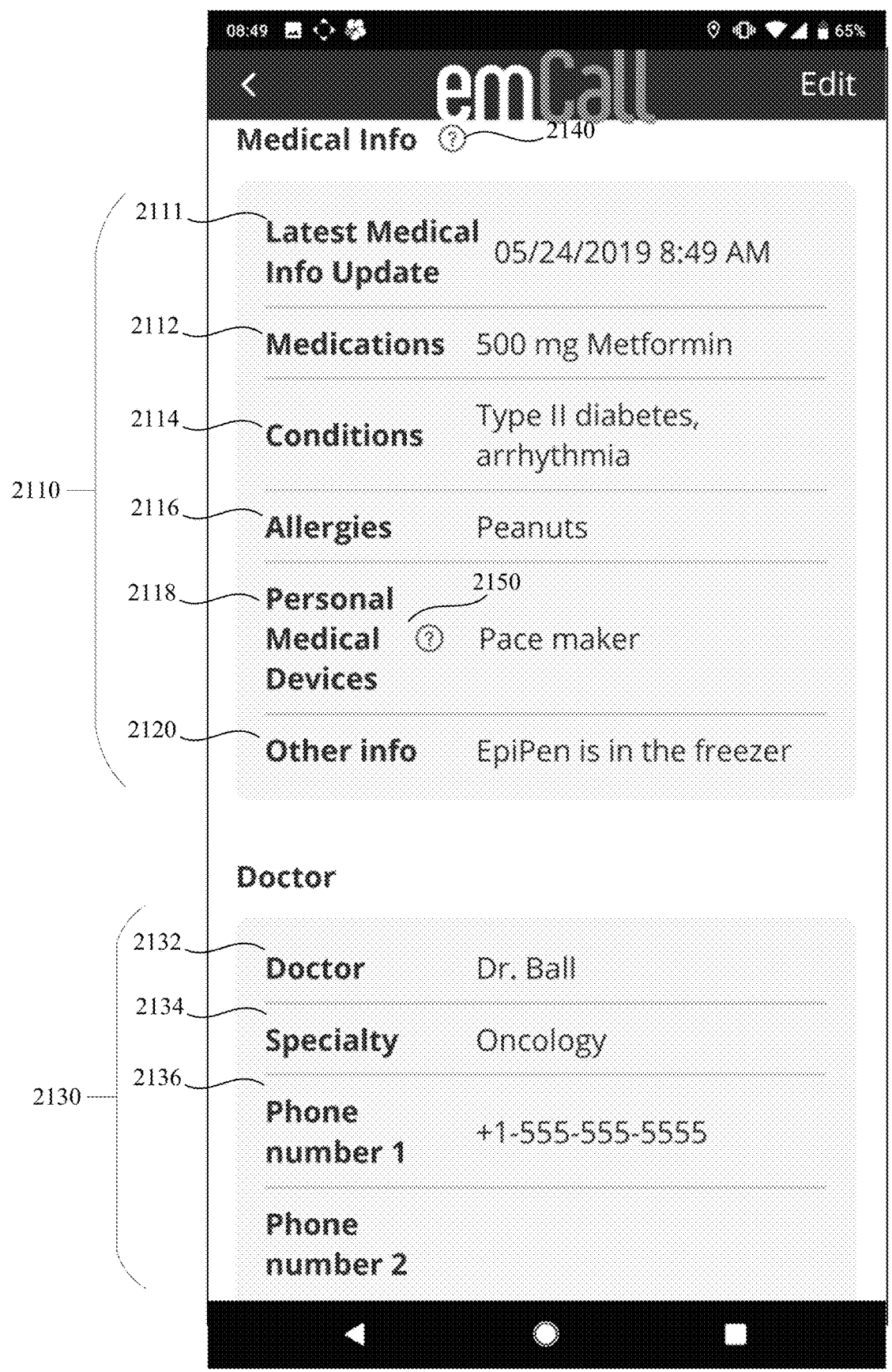
FIG. 21 illustrates a user interface for modifying a user profile in accordance with an exemplary embodiment of the present disclosure.
Figure 22A:
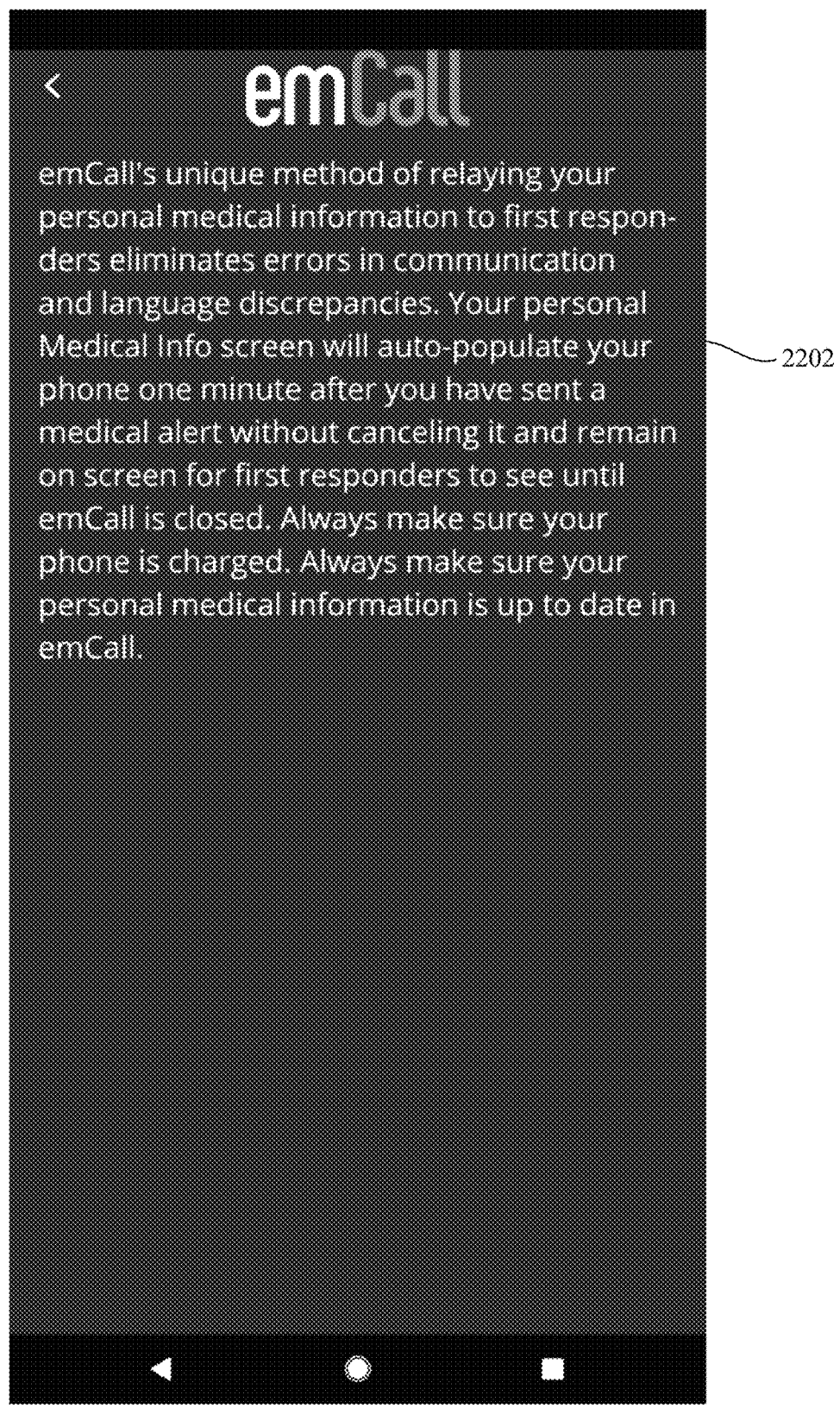
FIGS. 22A and 22B illustrate user interfaces for providing system information in accordance with exemplary embodiments of the present disclosure.
Figure 22B:
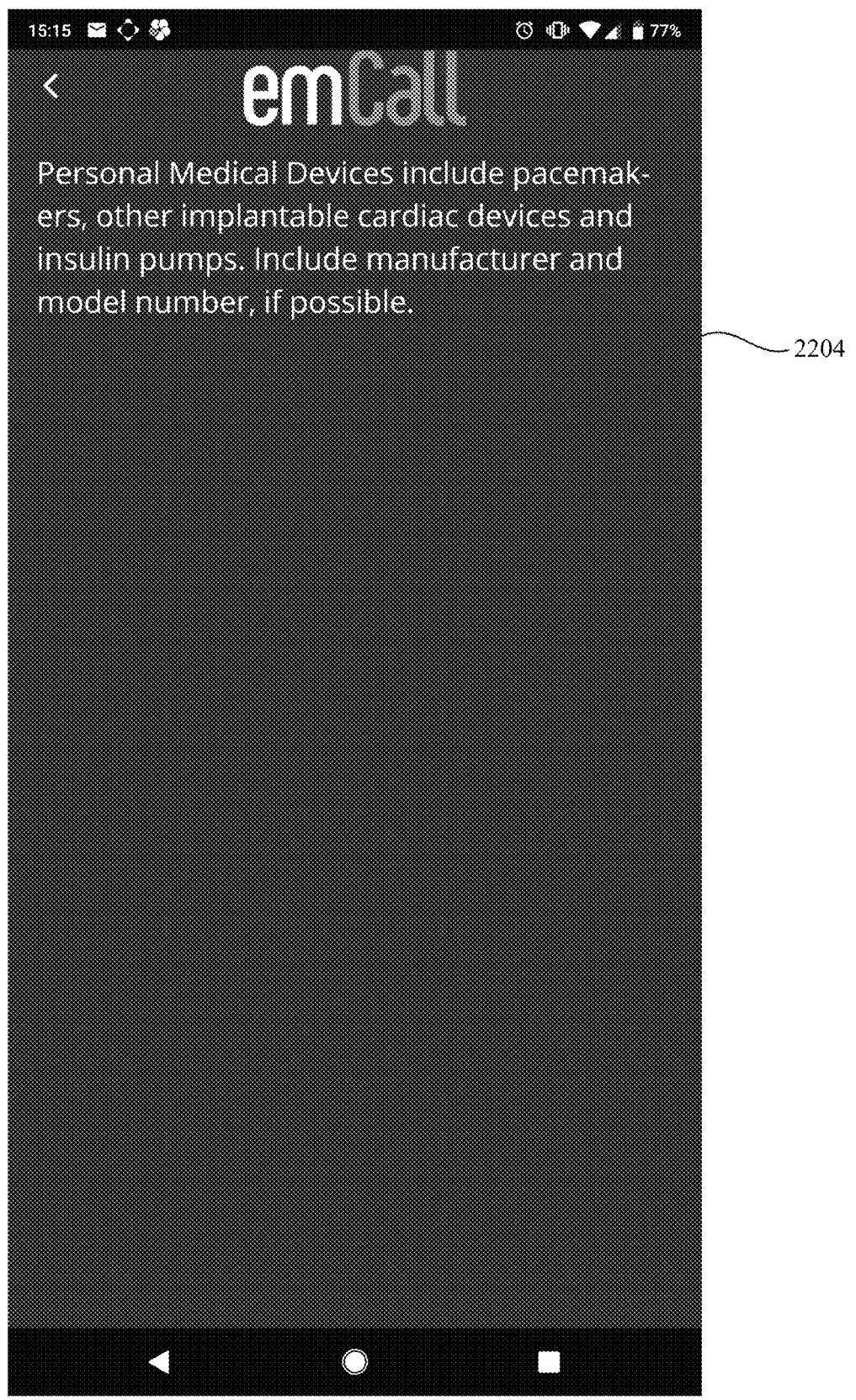

Referring briefly to FIG. 21, in some embodiments the medical information 2110 includes a latest medical information update 2111, which provides a time and/or a date that the latest medical information was updated or inputted to the health monitoring application 306 and/or the health monitoring and emergency support system 150. In some embodiments, if the end-user modifies any of the medical information fields (e.g., medical information 2110 and/or medical information 2130), or simply inputs (e.g., clicks, taps, etc.) on a field, the end-user is provided with a confirmation "e.g., an instruction to confirm YES or NO to saving recent medical information 2110 and/or 2130 changes). This confirmation is ensures that if the end-user intended to make any changes, those changes are registered (e.g., stored in health monitoring device 102, the health monitoring and emergency support system 150, an auxiliary server, etc.), rather than accidentally forgetting to store the information. In some embodiments, this confirmation applies to any information provided by the end-user of the health monitoring application (e.g., a confirmation if changing location notes 1610 and/or 1620; personal information fields 1810, 1820, and/or 1830; emergency information 1910, 1920, and/or 1930; etc.).

Figure 7B:

Referring to FIG. 7B, a GUI of a medical alert input 502 when sent to the health monitoring device 102 of the subject and remote device 104 associated with one or more support members is illustrated. A medical alert is typically an alert that is automatically sent for the subject (e.g., in accordance with an alarm trigger condition). In the embodiment illustrated in FIG. 7B, the user must press the medical alert input 502 three times to communicate the alert. However, the present disclosure is not limited thereto. For instance, in some embodiments the user must press the medical alert input 502 more than three times or in a predetermined sequence. As shown in FIG. 7B, the GUI includes information similar to that depicted in the GUI of FIG. 7A. However, the present disclosure is not limited thereto. In the embodiment illustrated in FIG. 7B, the volume indicator 510 is in a MUTE state and the network signal strength indicator 514 is lower than that of the network signal strength indicator 514 illustrated in FIG. 7A, as indicated by a number of concentric circle in the network signal strength indicator 514 with a higher number meaning a stronger signal.

Figure 9B:
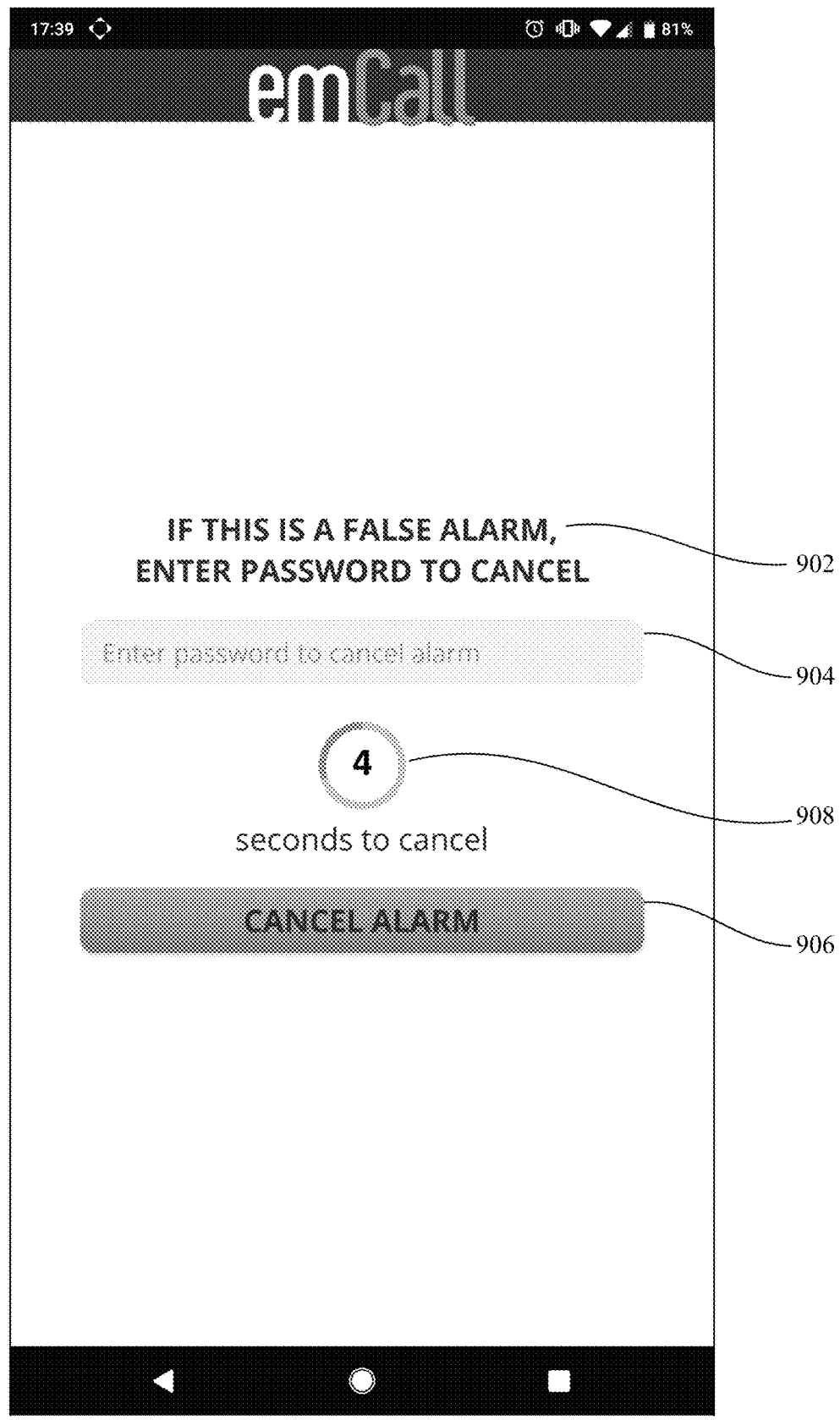
Figure 9C:
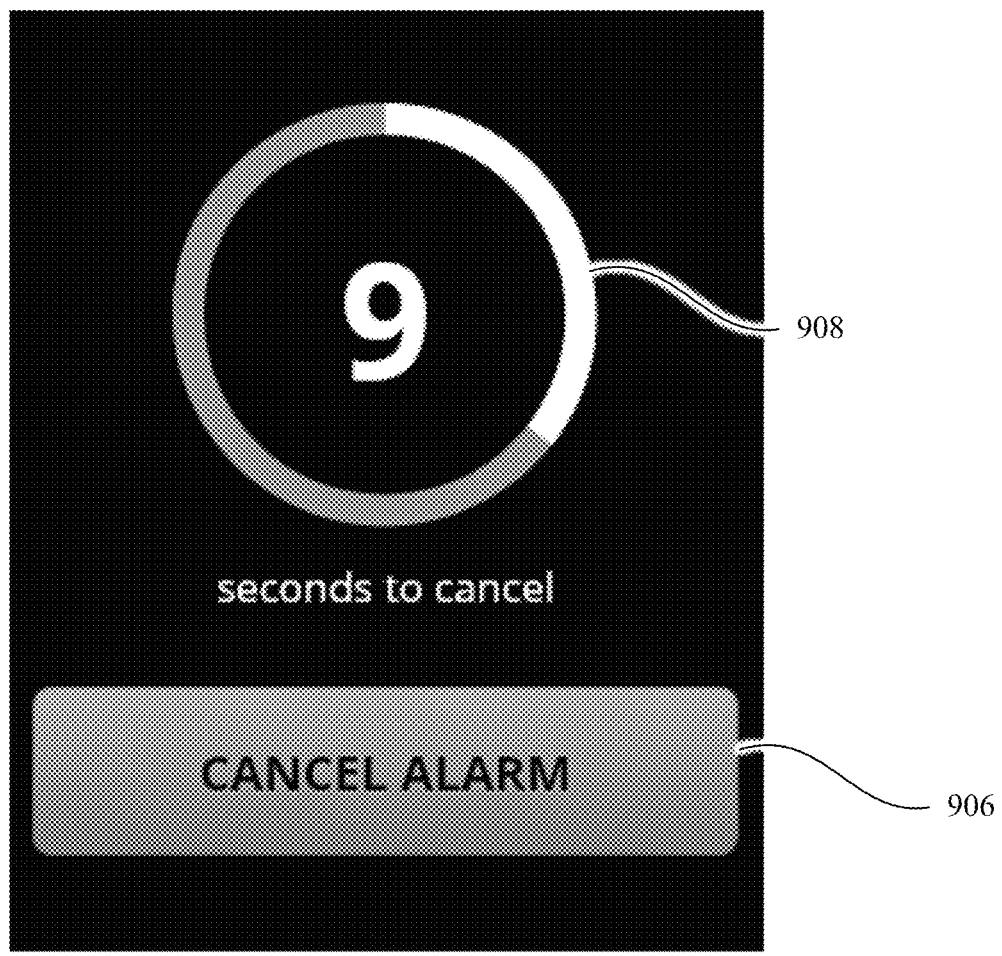

FIGS. 9A, 9B, and 9C illustrates various interruption methods. In the embodiment illustrated in FIG. 9A, the subject or support member must enter a predetermined password 701 within an allocated time period 702 in order to interrupt the alarm previously fired. In some embodiments, the time period 702 to interrupt the alarm is in a range of from one second to two minutes, two seconds to sixty seconds, two seconds to thirty seconds, five seconds to thirty seconds, five seconds to fifteen seconds, or a similar range of time. However, the present disclosure is not limited thereto. For instance, in some embodiments the user must press a button (e.g., button 906 of FIG. 9C) a number of times (e.g., three times) or more in a predetermined sequence to interrupt the alarm. In a further embodiment, the user must speak a first predetermined safe word (e.g., provide emergency information 1910 of FIG. 19 through a communication channel with the health monitoring and emergency support system 150, provided instruction 2000 of FIG. 20). In some embodiments, if the user uses a second safe word (e.g., an safe word other than the first predetermined safe word), this use is considered a verification of an alarm (e.g., S413 of FIG. 4). Allowing the subject or the support member to interrupt (e.g., reject) the alarm prevents false alarms from being communicated unnecessary to the remote alarm monitoring center.

Figure 10A:
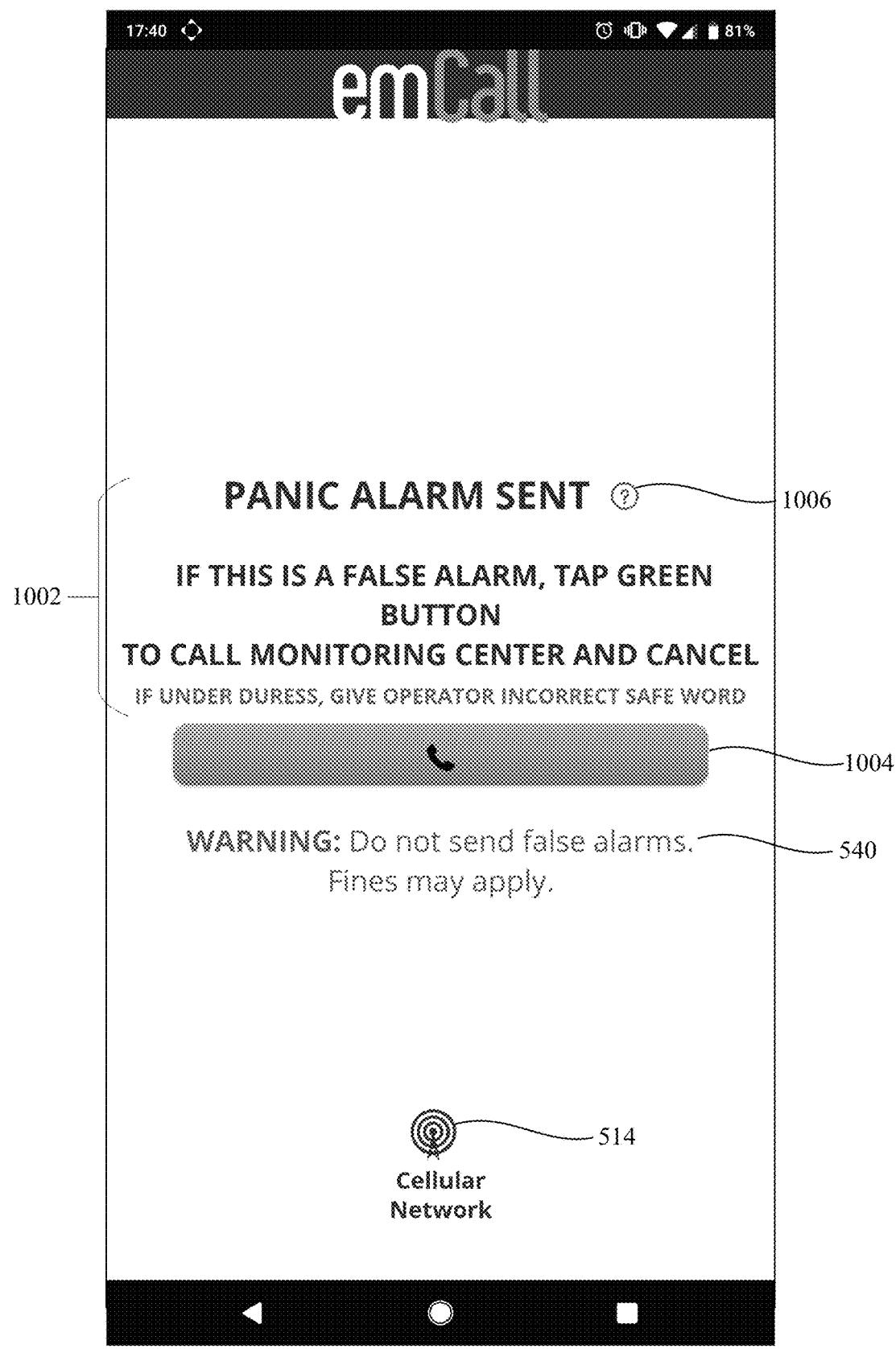
FIGS. 10A, 10B, and 10C illustrate user interfaces for communicating a panic alarm in accordance with exemplary embodiments of the present disclosure.
Figure 10B:
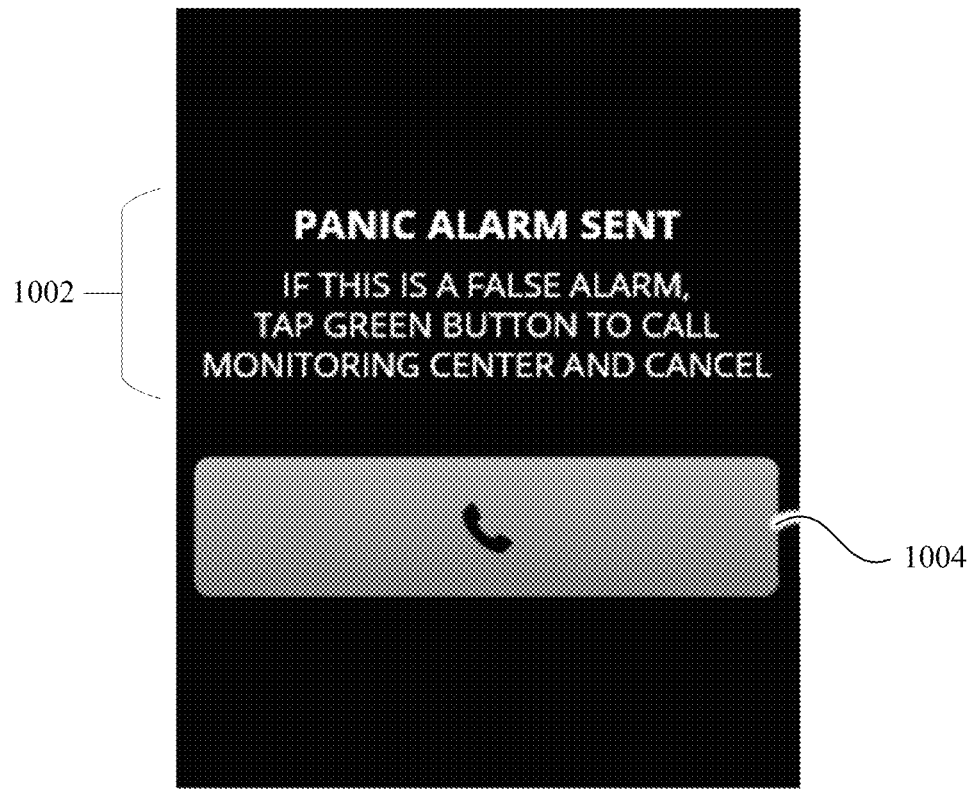
Figure 10C:
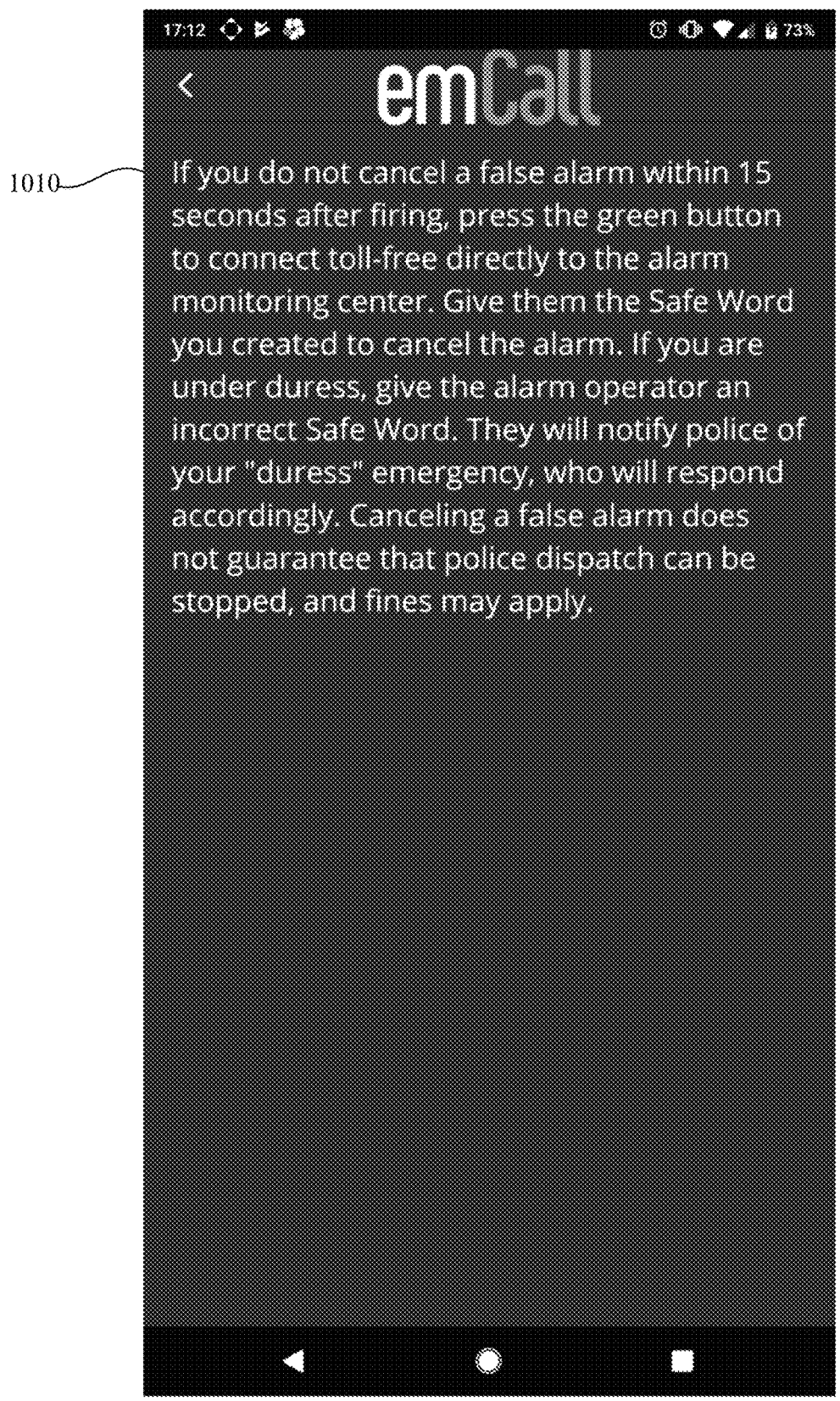
Figure 11A:
FIGS. 11A, 11B, and 11C illustrate user interfaces for communicating a medical alert in accordance with exemplary embodiments of the present disclosure.
Figure 11B:
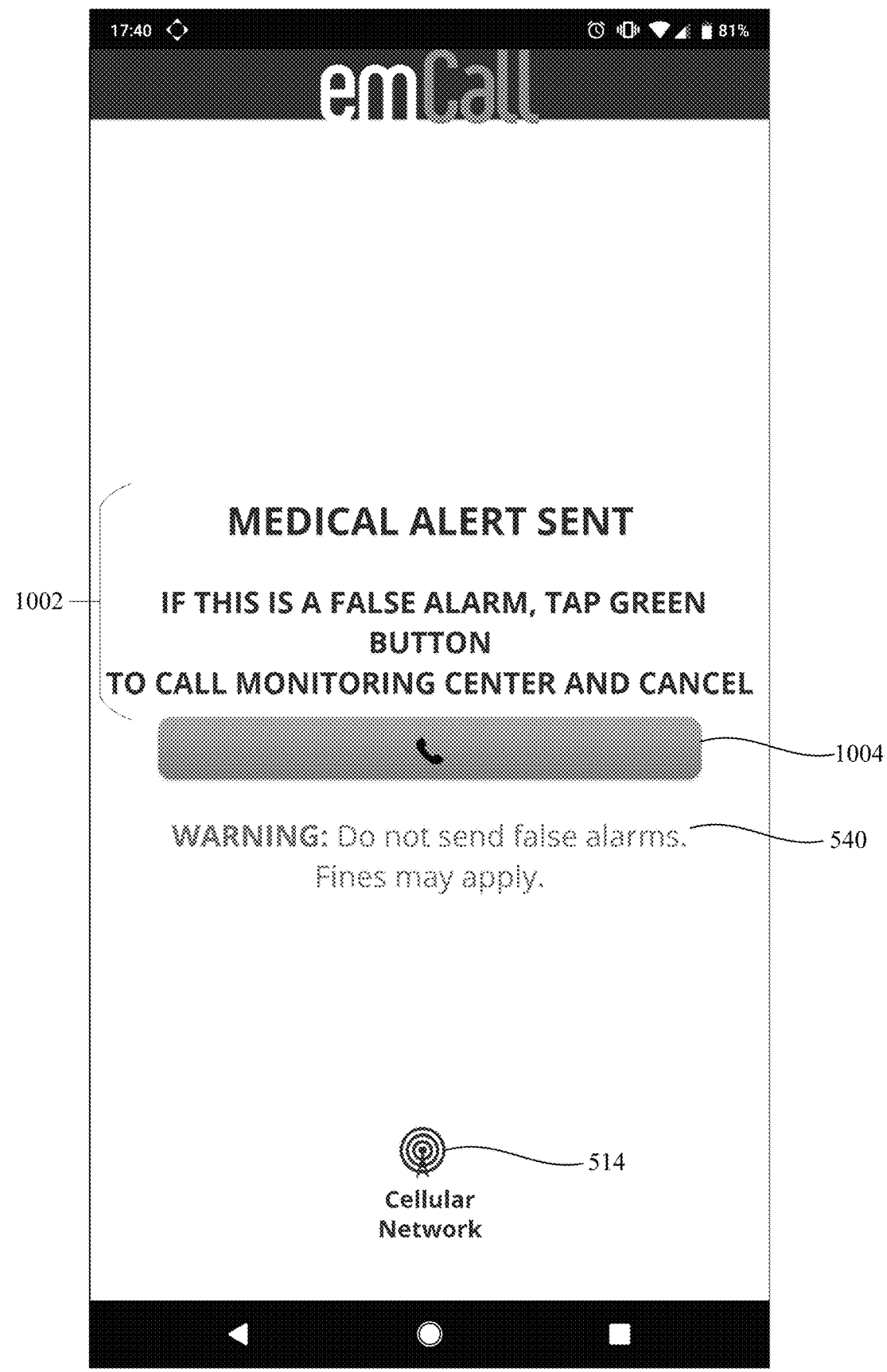
Figure 11C:
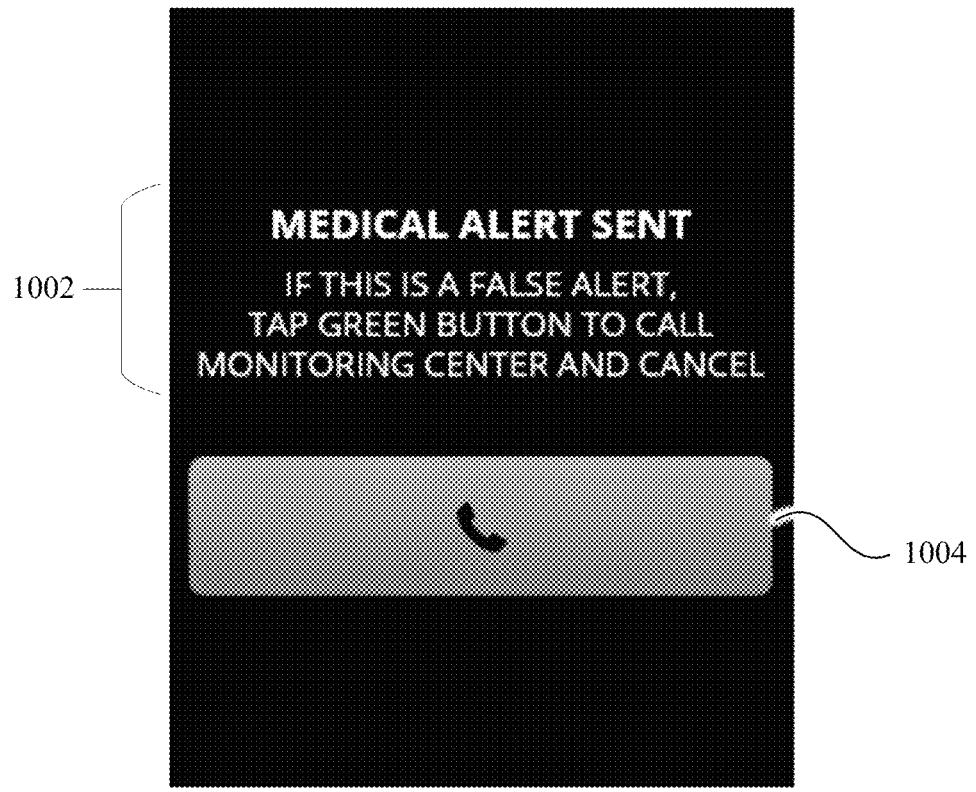

Referring to FIGS. 10A, 10B, and 10C various GUIs are illustrated for a fired panic alarm. In some embodiments, one the time period 702 has elapsed the health monitoring application 306 provides a GUI of FIG. 10A, 10B, or 10C which describe that the alarm has been communicated to the remote alarm monitoring center. These GUIs are typically displayed on the health monitoring device 102 until an emergency responder has arrived at the current location 702 of the health monitoring device. In some embodiments, the GUIs of FIG. 10A, 10B, or 10C provide a first assist icon 1006 that, upon interaction with the icon by the end-user of the health monitoring application, provides the instructions 1010 of FIG. 10C. In some embodiments, the GUIs of FIG. 10A, 10B, or 10C provide the end-user of the health monitoring application 306 the warning 540 regarding false alarms and/or the network strength indicator 514, allowing the end-user to, again, understand the consequences of firing an alarm and to verify that the alarm is communicated to the remote alarm monitoring center (e.g., through a graphical representation of a state of the network strength indicator 514 as described above). Referring briefly to FIG. 10C, in some embodiments the GUI provides an instruction 1010 describing how an end-user of the health monitoring device 102 can cancel (e.g., reject) a fired alarm (e.g., instructions for a subject to conduct S411 and/or S415 of FIG. 4). In some embodiments, the instruction 1010 includes a portion of the warning 540. FIG. 11A illustrates a GUI of another interruption method where the user must call a phone number 1004 to interrupt the alarm (e.g., the end-user of the health monitoring application 306 must call 1004 in order to reject the alarm (e.g., S411 and/or S415 of FIG. 4)).

Figure 13:
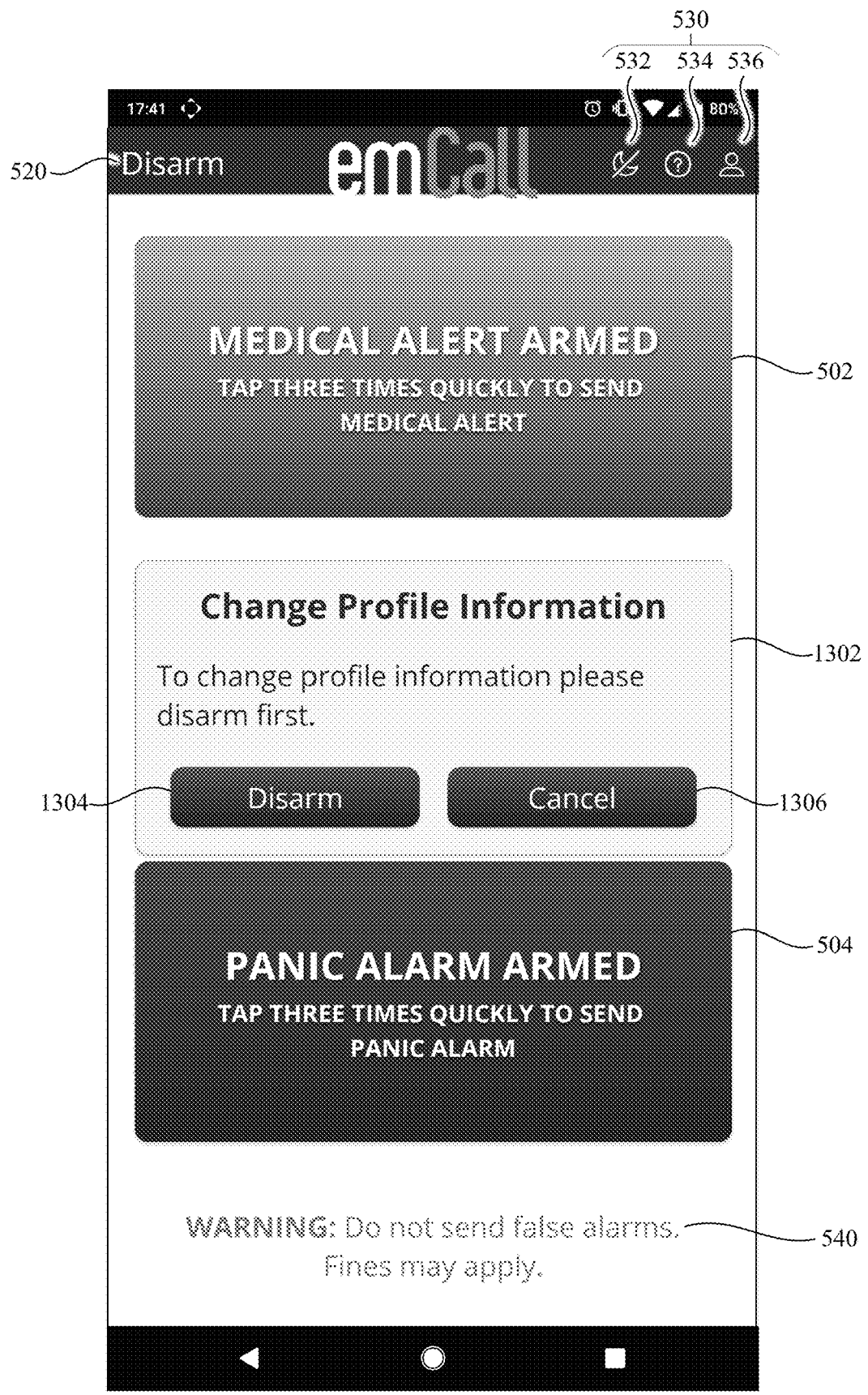
FIG. 13 illustrates a user interface for modifying a profile of a health monitoring application in accordance with an exemplary embodiment of the present disclosure.

Referring to FIG. 13, a GUI of a health monitoring application in an armed state is illustrated. In some embodiments, since the health monitoring application 306 is in an armed state the end-user must disarm the application 306 to change various information within the application (e.g., application settings 1520 and/or location notes 1510 of FIG. 15).

Figure 14:
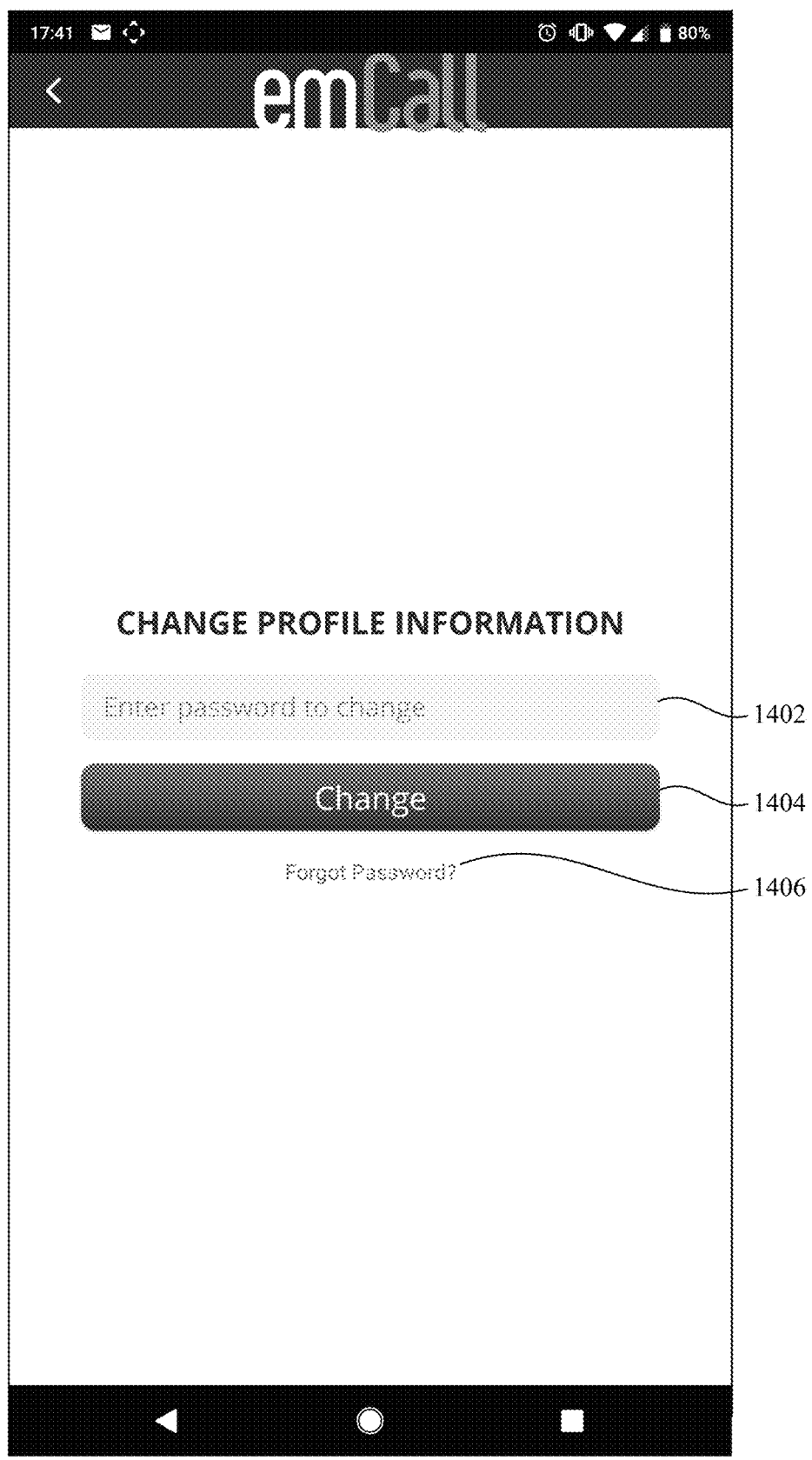
FIG. 14 illustrates a user interface for modifying a profile of a health monitoring application in accordance with an exemplary embodiment of the present disclosure.
Figure 15:
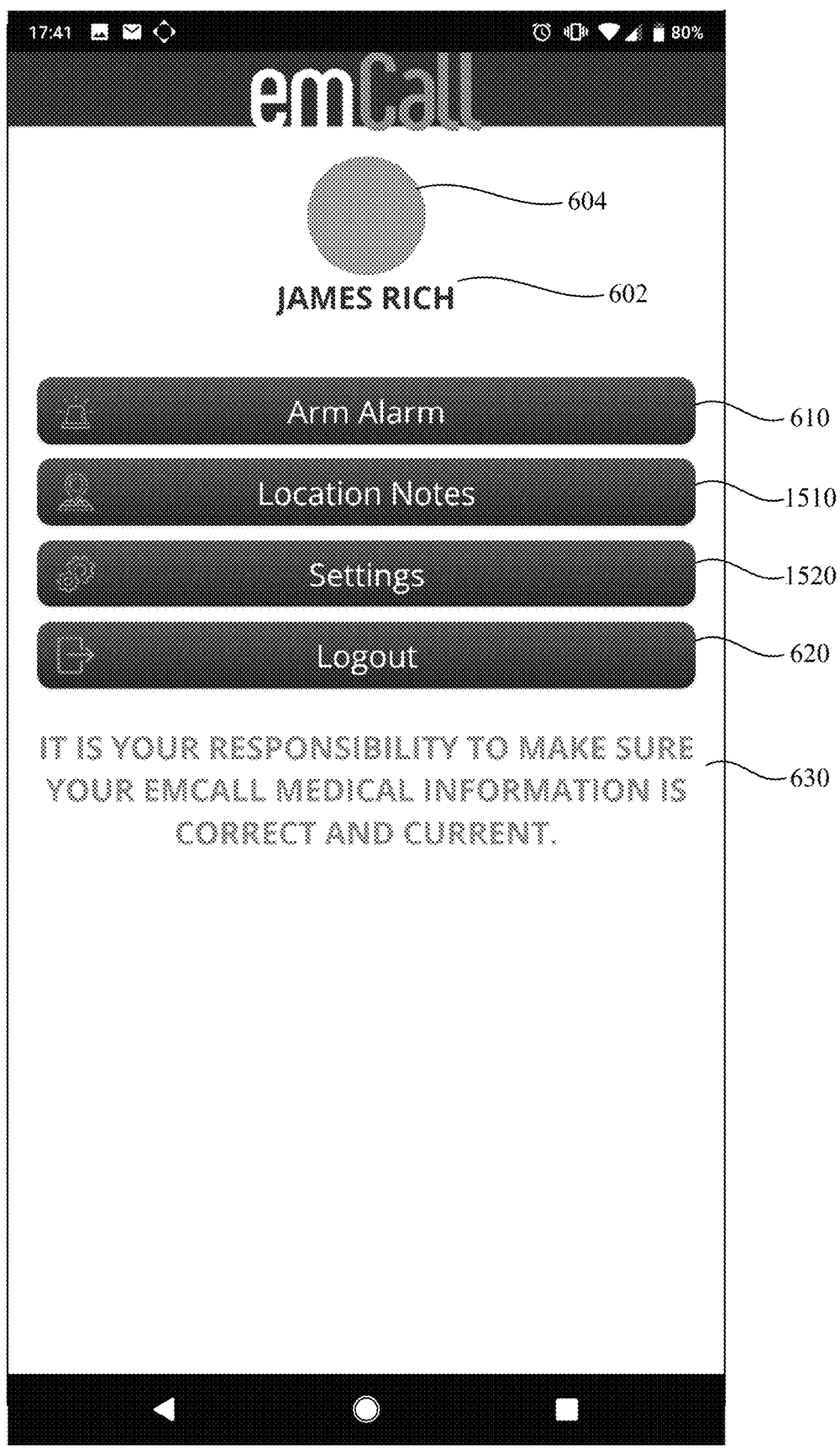
FIG. 15 illustrates a user interface for modifying a profile of a health monitoring application in accordance with an exemplary embodiment of the present disclosure.
Figure 16:
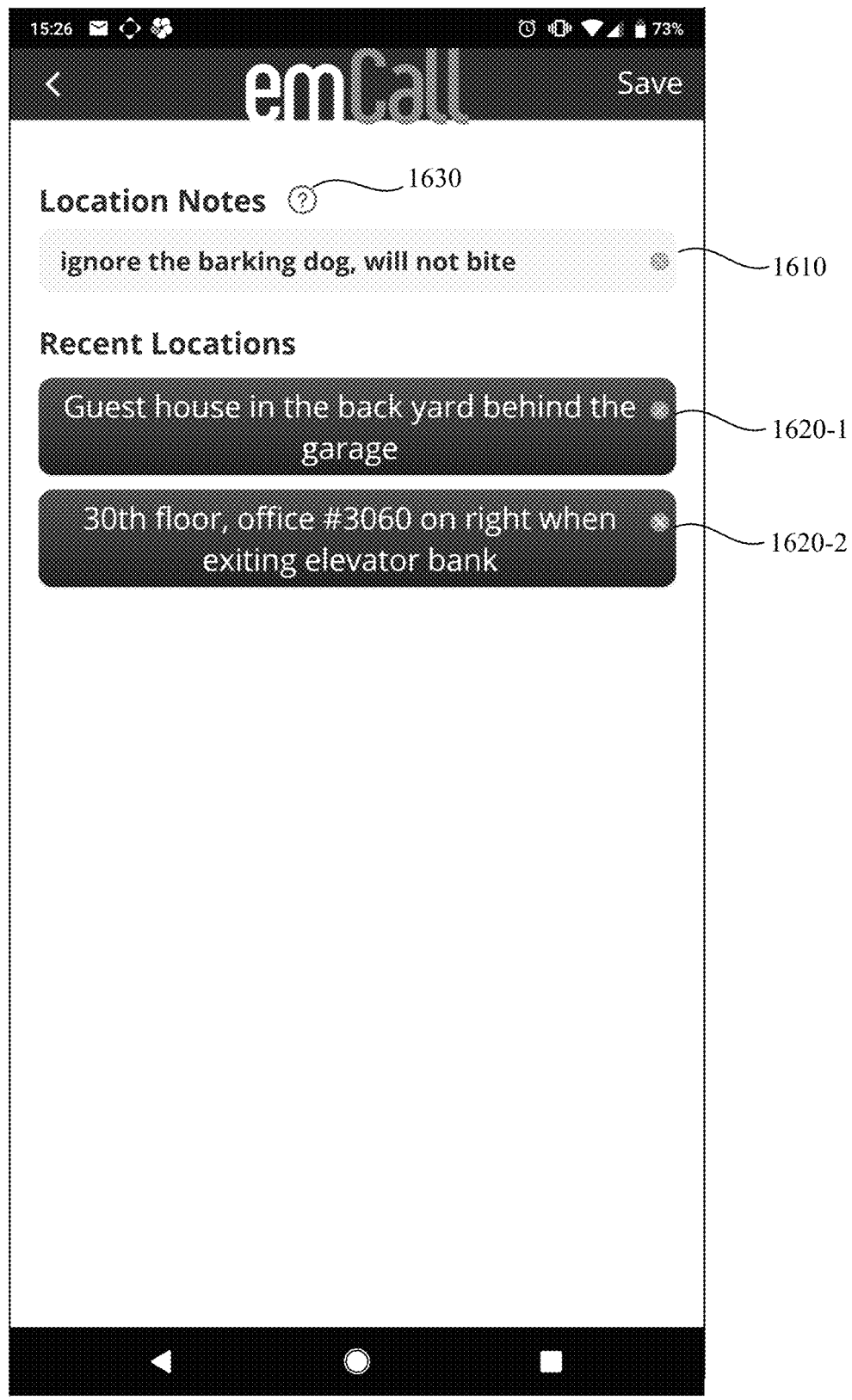
FIG. 16 illustrates a user interface for modifying location settings of a health monitoring application in accordance with an exemplary embodiment of the present disclosure.

Referring to FIG. 14, in some embodiments once the health monitoring application 306 is in a disarmed state, the end-user is allowed to modify settings of the health monitoring application (e.g., user settings module 320 and/or application settings module 322 of FIG. 3), such as modifying 14014 a password 1402. In some embodiments, the end-user must enter a password and/or an email address (e.g., account information 2310 and/or login information 2320 of FIG. 23) to modify settings of the health monitoring application 306.

Figure 24:
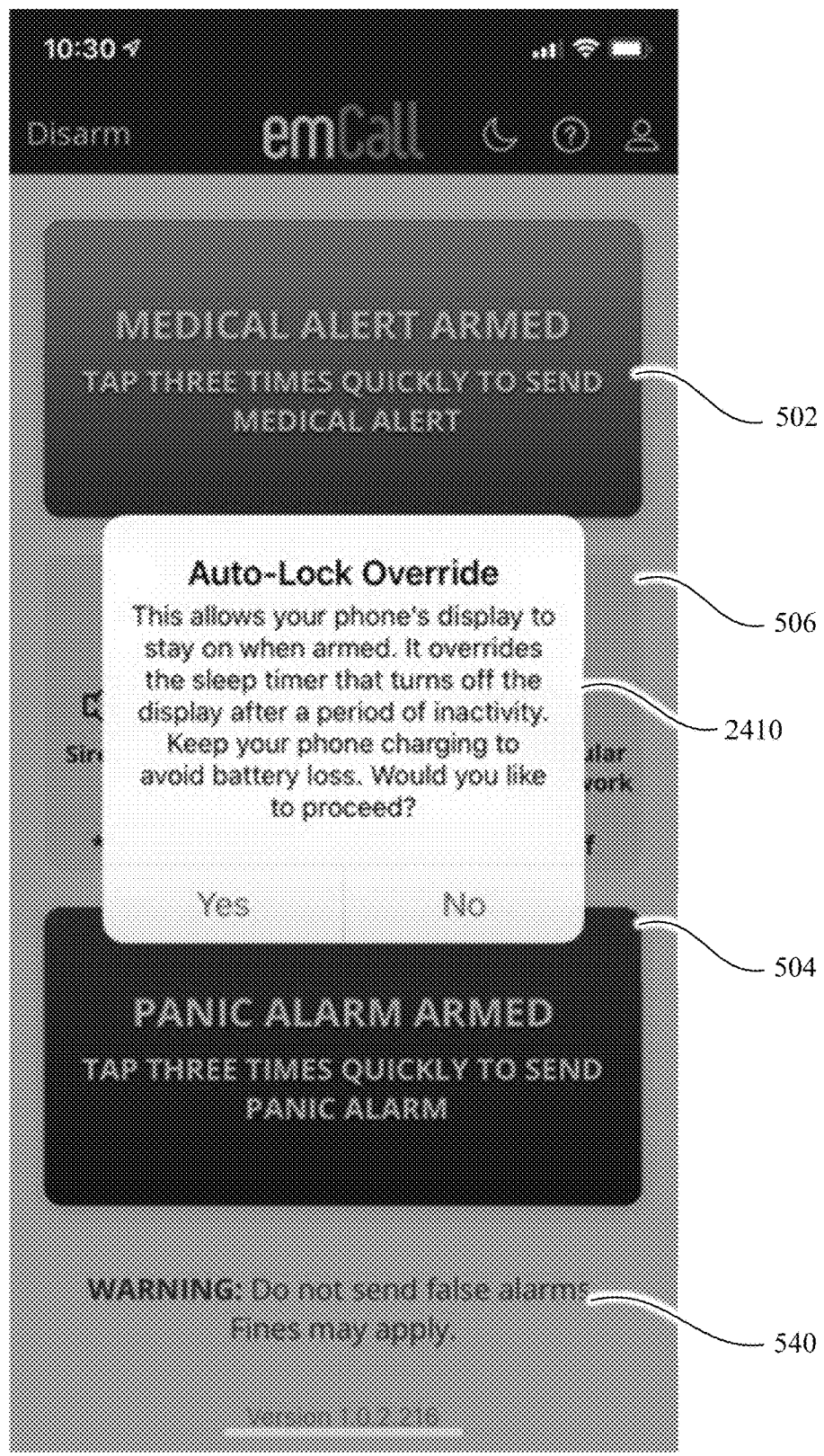
FIG. 24 illustrates a user interface for a health monitoring application in accordance with an exemplary embodiment of the present disclosure.

Referring to FIG. 24, in some embodiments the end-user of the health monitoring application 306 is provided with a prompt 2410 to override a setting of the health monitoring device 102 (e.g., a display setting, a volume setting, a location setting, etc.). In some embodiments, the prompt is to override a display setting of the health monitoring device 102, such that the display (e.g., display 376 of FIG. 3) is ON (e.g., in an illuminated state) when the health monitoring application 306 is armed. In some embodiments, the override of the display setting configures the health monitoring device 102 to turn the display (e.g., display 376 of FIG. 3) ON or in an illuminated state (e.g., an awake state) in accordance with a detected input (e.g., data from accelerometer 397 and/or optical sensor 368 of FIG. 3). In some embodiments, this display override allows the display of the health monitoring device 102 to stay illuminated when armed, such that a default timer that turns OFF the display after a period of inactivity is void. This display override accommodates subjects who want the display of the health monitoring device 102 constantly illuminated so that the health monitoring application 306 is available immediately without having to unlock the health monitoring device 102, navigate to the health monitoring application 306, and trigger an alarm (e.g., S419 of FIG. 4). For instance, if the subject is jogging and needs to fire an alert (e.g., S419 of FIG. 4), the subject may move (e.g., provide an input to receive data from the accelerometer 397 of FIG. 3) the health monitoring device 102 to illuminate the display, which provides a GUI to fire an alarm (e.g., provides the GUI of FIG. 8A through 8D. This configuration provides the avoidance of having to navigate through layers of screens to arrive the appropriate GUI to fire an alarm during an emergency situation (e.g., the subject is provide a simply and fast mechanism to input S419 of FIG. 4).

Accordingly, a health monitoring and emergency support service according to an exemplary embodiment of the present disclosure achieves the advantages of streamlining the process of dispatching emergency responders, engaging a subject's circle of support, and supplying the emergency responders with critical patient medical information while minimizing or eliminating the number of false calls. The current location of the subject is can be provided to the subject's circle of support and a remote alarm monitoring center, allowing emergency support to be provided to the subject even if the subject is incapacitated.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various alternatives and modifications thereof. It is intended that the scope of the invention be defined by the Claims appended hereto and their equivalents.

What is claimed is:

1. A computer system for providing a health monitoring and emergency support service to a plurality of subjects, the computer system comprising:
  at a first computer comprising one or more first processors and a first memory, the first memory comprising first non-transitory instructions which, when executed by the one or more first processors, performs a first method comprising:
  running a monitoring process, wherein, for each respective subject in the plurality of subjects, the monitoring process comprises:
   (i) polling for a respective data element in a plurality of data elements from a corresponding health monitoring device in a plurality of health monitoring devices associated with the respective subject,
   (ii) initiating a first notification process for a candidate subject in the plurality of subjects when the respective data element satisfies a first alarm trigger condition, wherein the first notification process, performed for the candidate subject in the plurality of subjects when the respective data element satisfies the first alarm trigger condition, comprises notifying a remote alarm monitoring center about the first alarm trigger condition and a current location of the candidate subject, and
   (iii) initiating a second notification process for the candidate subject in the plurality of subjects when the respective data element satisfies a second alarm trigger condition, wherein the second notification process, performed for the candidate subject in the plurality of subjects when the respective data element satisfies the second alarm trigger condition, comprises:
  communicating the data element or the second alarm trigger condition to each remote device in a plurality of remote devices, wherein each remote device in the plurality of remote devices is associated with a respective support member in a plurality of support members, and wherein each respective support member is uniquely associated with the candidate subject;
  communicating the data element or the second alarm trigger condition to the corresponding health monitoring device associated with the candidate subject;
  concurrently polling for a verification response from the plurality of remote devices and the health monitoring device associated with the candidate subject; and
  responsive to receiving the verification response from either (i) any one or more remote devices in the plurality of remote devices or (ii) from and the health monitoring device associated with the candidate subject:
initiating a third notification process that notifies the remote alarm monitoring center about the second alarm trigger condition and the current location of the candidate subject when the verification response satisfies a first condition, and
terminating the second notification process when the verification response satisfies a second condition without notifying the remote alarm monitoring center about the second alarm trigger condition, wherein:
the first condition is satisfied in accordance with a determination that a most recently received verification response from one or more remote devices in the plurality of remote devices is a confirmation,
the first condition is satisfied in accordance with a determination that a most recently received verification response from the health monitoring device associated with the candidate subject is a confirmation, and
the second condition is satisfied in accordance with a determination that a most recently received verification response from either (i) any one or more remote devices in the plurality of remote devices or (ii) the health monitoring device associated with the candidate subject is a rejection.

2. The system of claim 1, wherein the first notification process further comprises communicating the data element or the first alarm trigger condition to each remote device in the plurality of remote devices.

3. The system of claim 1, wherein satisfying the first alarm trigger condition includes through one or more commands by either the candidate subject or a respective remote device in the plurality of remote devices.

4. The system of claim 1, wherein the polling further comprises instructions for receiving an interrupt communication from the candidate subject, wherein when the interrupt communication from the candidate subject is received within a predetermined time period of receiving the respective data element for the candidate subject, the respective notification process and the respective alarm trigger condition are cancelled.

5. The system of claim 4, wherein the instructions for receiving the interrupt communication from the candidate subject further comprises: when the interrupt communication from the candidate subject is not received the predetermined time period of receiving the respective data element for the candidate subject, a communication channel is opened between the candidate subject and the remote alarm monitoring center.

6. The system of claim 5, wherein the communication channel requires entry of a password in order to remain open.

7. The system of claim 6, wherein the interrupt communication from the candidate subject is confirmed through entry of the password.

8. The system of claim 6, wherein the password is a spoken safe word.

9. The system of claim 1, wherein the current location of the candidate subject comprises a set of geographical coordinates including a latitude, a longitude, and/or an elevation.

10. The system of claim 1, wherein the current location of the candidate subject comprises a physical address.

11. The system of claim 1, wherein the current location of the candidate subject includes one or more instructions provided by the candidate subject.

12. The system of claim 1, wherein the notifying the remote alarm monitoring center comprises providing the current location of the candidate subject on a recurring basis.

13. The system of claim 1, wherein the second notification process further comprises creating a communication channel between the candidate subject and each respective support member in the plurality of support members independent of a location of the respective support member responsive to the alarm trigger condition, wherein the communication channel allows for the candidate subject and a respective support member to directly communicate with each other.

14. The system of claim 1, wherein the second notification process further comprises creating a communication channel between the candidate subject and the remote alarm monitoring center responsive to the alarm trigger condition, wherein the communication channel allows for the candidate subject and the remote alarm monitoring center to directly communicate with each other.

15. The system of claim 1, wherein the third notification process further comprises creating a communication channel between the candidate subject and the remote alarm monitoring center responsive to the alarm trigger condition, wherein the communication channel allows for the candidate subject and the remote alarm monitoring center to directly communicate with each other.

16. The system of claim 1, wherein the third notification process further comprises communicating a plurality of medical information related to the candidate subject to each remote device in the plurality of remote devices and the health monitoring device associated with the candidate subject.

17. The system of claim 16, wherein the plurality of medical information is provided through a link to a third-party website.

18. The system of claim 1, wherein the first notification process further comprises notifying the remote alarm monitoring center about a state of a volume setting of the health monitoring device.

19. A non-transitory computer readable storage medium, wherein the non-transitory computer readable storage medium stores instructions, which when executed by a computer system, cause the computer system to perform a method for providing a health monitoring and emergency support service, the method comprising:
running a monitoring process, wherein, for each respective subject in the plurality of subjects, the monitoring process comprises:
(i) polling for a respective data element in a plurality of data elements from a corresponding health monitoring device in a plurality of health monitoring devices associated with the respective subject,
(ii) initiating a first notification process for a candidate subject in the plurality of subjects when the respective data element satisfies a first alarm trigger condition, wherein the first notification process, performed for the candidate subject in the plurality of subjects when the respective data element satisfies the first alarm trigger condition, comprises notifying a remote alarm monitoring center about the first alarm trigger condition and a current location of the candidate subject, and
(iii) initiating a second notification process for the candidate subject in the plurality of subjects when the respective data element satisfies a second alarm trigger condition, wherein the second notification process, performed for the candidate subject in the plurality of subjects when the respective data element satisfies the second alarm trigger condition, comprises:
communicating the data element or the second alarm trigger condition to each remote device in a plurality of remote devices, wherein each remote device in the plurality of remote devices is associated with a respective support member in a plurality of support members, and wherein each respective support member is uniquely associated with the candidate subject;
communicating the data element or the second alarm trigger condition to the corresponding health monitoring device associated with the candidate subject;
concurrently polling for a verification response from the plurality of remote devices and the health monitoring device associated with the candidate subject; and
responsive to receiving the verification response from either (i) any one or more remote devices in the plurality of remote devices or (ii) from and the health monitoring device associated with the candidate subject:
initiating a third notification process that notifies the remote alarm monitoring center about the second alarm trigger condition and the current location of the candidate subject when the verification response satisfies a first condition, and
terminating the second notification process when the verification response satisfies a second condition without notifying the remote alarm monitoring center about the second alarm trigger condition, wherein:
the first condition is satisfied in accordance with a determination that a most recently received verification response from one or more remote devices in the plurality of remote devices is a confirmation,
the first condition is satisfied in accordance with a determination that a most recently received verification response from the health monitoring device associated with the candidate subject is a confirmation, and
the second condition is satisfied in accordance with a determination that a most recently received verification response from either (i) any one or more remote devices in the plurality of remote devices or (ii) the health monitoring device associated with the candidate subject is a rejection.

20. A method for providing a health monitoring and emergency support service to a plurality of subjects, the method comprising:
at a first computer comprising one or more first processors and a first memory, the first memory comprising first non-transitory instructions which, when executed by the one or more first processors, performs a first method comprising:
running a monitoring process, wherein, for each respective subject in the plurality of subjects, the monitoring process comprises:
(i) polling for a respective data element in a plurality of data elements from a corresponding health monitoring device in a plurality of health monitoring devices associated with the respective subject,
(ii) initiating a first notification process for a candidate subject in the plurality of subjects when the respective data element satisfies a first alarm trigger condition, wherein the first notification process, performed for the candidate subject in the plurality of subjects when the respective data element satisfies the first alarm trigger condition, comprises notifying a remote alarm monitoring center about the first alarm trigger condition and a current location of the candidate subject, and
(iii) initiating a second notification process for the candidate subject in the plurality of subjects when the respective data element satisfies a second alarm trigger condition, wherein the second notification process, performed for the candidate subject in the plurality of subjects when the respective data element satisfies the second alarm trigger condition, comprises:
communicating the data element or the second alarm trigger condition to each remote device in a plurality of remote devices, wherein each remote device in the plurality of remote devices is associated with a respective support member in a plurality of support members, and wherein each respective support member is uniquely associated with the candidate subject;
communicating the data element or the second alarm trigger condition to the corresponding health monitoring device associated with the candidate subject;
concurrently polling for a verification response from the plurality of remote devices and the health monitoring device associated with the candidate subject; and
responsive to receiving the verification response from either (i) any one or more remote devices in the plurality of remote devices or (ii) from and the health monitoring device associated with the candidate subject:
initiating a third notification process that notifies the remote alarm monitoring center about the second alarm trigger condition and the current location of the candidate subject when the verification response satisfies a first condition, and
terminating the second notification process when the verification response satisfies a second condition without notifying the remote alarm monitoring center about the second alarm trigger condition, wherein:
the first condition is satisfied in accordance with a determination that a most recently received verification response from one or more remote devices in the plurality of remote devices is a confirmation,
the first condition is satisfied in accordance with a determination that a most recently received verification response from the health monitoring device associated with the candidate subject is a confirmation, and
the second condition is satisfied in accordance with a determination that a most recently received verification response from either (i) any one or more remote devices in the plurality of remote devices or (ii) the health monitoring device associated with the candidate subject is a rejection.

* * * * *